United States Patent
Yoon et al.

(10) Patent No.: US 12,263,196 B2
(45) Date of Patent: Apr. 1, 2025

(54) **COMPOSITIONS AND METHODS FOR INHIBITING THE PROLIFERATION OF ENTEROTOXIGENIC *BACTEROIDES FRAGILIS***

(71) Applicant: iNtRON Biotechnology, Inc., Gyeonggi-do (KR)

(72) Inventors: Seong Jun Yoon, Seoul (KR); Jee Soo Son, Seoul (KR); In Hwang Kim, Gyeonggi-do (KR); Hyoung Rok Paik, Incheon (KR); Eun Kyoung Oh, Gyeonggi-do (KR); Soo Youn Jun, Seoul (KR); Sang Hyeon Kang, Seoul (KR)

(73) Assignee: iNtRON Biotechnology, Inc., Gyeonggi-do (KR)

( * ) Notice: Subject to any disclaimer, the term of this patent is extended or adjusted under 35 U.S.C. 154(b) by 0 days.

(21) Appl. No.: 18/490,521

(22) Filed: Oct. 19, 2023

(65) Prior Publication Data

US 2024/0041958 A1    Feb. 8, 2024

Related U.S. Application Data

(63) Continuation of application No. 17/227,284, filed on Apr. 10, 2021, now abandoned.

(51) Int. Cl.
*A61K 35/76* (2015.01)
*A61P 31/04* (2006.01)

(52) U.S. Cl.
CPC .............. *A61K 35/76* (2013.01); *A61P 31/04* (2018.01)

(58) Field of Classification Search
None
See application file for complete search history.

(56) References Cited

FOREIGN PATENT DOCUMENTS

WO    WO-2014070225 A1 *  5/2014  ........... A61K 35/742

OTHER PUBLICATIONS

Tariq, M.A. et al. 2020. Genome characterization of a novel wastewater Bacteroides fragilis bacteriophase (vB_BfrS_23) and its host GB124. Frontiers in Microbiology 11: 1-12 w Supplementary data; specif. pp. 1, 4, 10 (Year: 2020).*
NCBI Blast sequence search. SEQ ID No. 1. Datasheet [online]. Retrieved on Aug. 2, 2024. Downloaded from the internet: <https: www.ncbi.nlm.gov/nucleotide/MT630433.1?report=genbank&log$=nucltop&blast_rank=19&RID=ATGY40CU13>. pp. 1-3 (Year: 2024).*

* cited by examiner

*Primary Examiner* — Adam Weidner
*Assistant Examiner* — Sharon M. Papciak
(74) *Attorney, Agent, or Firm* — SIMI Law Group, P.C.

(57) ABSTRACT

A composition for preventing or treating an infection or disease caused by enterotoxigenic *Bacteroides fragilis* includes a Siphoviridae bacteriophage (Bac-FRP-3) having an ability to lyse the enterotoxigenic *Bacteroides fragilis* cells and a pharmaceutically acceptable carrier. A method for preventing or treating an infection or disease caused by enterotoxigenic *Bacteroides fragilis* includes administering to a subject a Siphoviridae bacteriophage and lysing the enterotoxigenic *Bacteroides fragilis* cells by the Siphoviridae bacteriophage.

5 Claims, 4 Drawing Sheets

Specification includes a Sequence Listing.

COMPOSITIONS AND METHODS FOR INHIBITING THE PROLIFERATION OF ENTEROTOXIGENIC *BACTEROIDES FRAGILIS*

This application is a Continuation Application of U.S. Ser. No. 17/227,284, filed on Apr. 10, 2021, which is incorporated by reference for all purposes as if fully set forth herein. A Sequence Listing XML file named "20001_0059C1.xml" created on Oct. 19, 2023, and having a size of 47,615 bytes, is filed concurrently with the specification. The sequence listing contained in the XML file is part of the specification and is herein incorporated by reference in its entirety.

BACKGROUND OF THE INVENTION

Field of the Invention

The present invention relates to compositions and methods for inhibiting the proliferation of enterotoxigenic *Bacteroides fragilis*, more specifically, a composition containing a Siphoviridae bacteriophage and a method of using the same.

Discussion of the Related Art

*Bacteroides* species comprise nearly half of the fecal flora community and are host symbionts critical to host nutrition and mucosal and systemic immunity. Among *Bacteroides* species, *Bacteroides fragilis* (*B. fragilis*) strains are opportunistic pathogens. Enterotoxigenic *B. fragilis* (ETBF) can produce a proteolytic enterotoxin, named as *B. fragilis* enterotoxin (BFT), or fragilysin, that causes secretory diarrhea and colonic epithelial damage. ETBF emerged over the past 35 years as a global etiology of diarrheal disease in animals and humans that is accompanied by colitis (Clin. Microbiol. Rev. 22: 349-369, 2009). An association of ETBF with chronic intestinal disease has been established for more than 20 years and ETBF is also positively associated with ulcerative colitis and colonic neoplasia (Gut Pathog. 9: 53-59, 2017; BMC Canc. 19: 879-882, 2019).

In addition, ETBF may cause cancer such as colorectal cancer (CRC). CRC is one of the most common cancers, accounting for approximately 10% of all cancer cases and approximately 8% of all cancer deaths. BFT is known to bind to colonic epithelial cells (CECs) and to stimulate cleavage of the tumor suppressor protein, E-cadherin. E-cadherin cleavage increases intestinal barrier permeability and augments cell signaling via the β-catenin/Wnt pathway which is constitutively activated in essentially all CRC. As a result, BFT stimulates proliferation and migration of human colon cancer cells in vitro (Gastroenterology 124: 392-400, 2003). The ability of BFT to further activate the nuclear factor-kappaB (NF-κB) pathway inducing pro-inflammatory cytokine secretion by CECs and data indicating that specific pools of NF-κB foster the initiation and promotion of epithelial tumorigenesis led to the hypothesis that ETBF were pro-inflammatory, oncogenic colonic bacteria. This hypothesis was supported by a recent small study in Turkey suggesting that ETBF colonization is more frequent in CRC patients than in controls without CRC (Clin. Microbiol. Infect. 12: 782-786, 2006).

Generally, antibiotics are used for the treatment of infectious diseases of ETBF. Here, the effectiveness of antibiotics has been continuously decreasing due to the increase of antibiotic-resistant ETBF, and the development of effective methods other than currently prescribed antibiotics is required.

Recently, the use of bacteriophages as a countermeasure against bacterial infectious diseases has attracted considerable attention. Bacteriophages are very small microorganisms infecting bacteria, and are usually simply called "phages." Once a bacteriophage infects a bacterial cell, the bacteriophage is proliferated inside the bacterial cell. After proliferation, the progeny of the bacteriophage destroys the bacterial cell wall and escapes from the host bacteria, suggesting that the bacteriophage has the ability to kill bacteria. The manner in which the bacteriophage infects bacteria is characterized by the very high specificity thereof, and thus the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria, but does not affect commensal bacteria in animals including human being. Conventional antibiotics, which have been widely used for bacterial treatment, incidentally influence many kinds of bacteria. This causes problems such as the disturbance of normal microflora. On the other hand, the use of bacteriophages does not disturb normal microflora, because the target bacterium is selectively killed. Hence, the bacteriophage may be utilized safely, which thus greatly lessens the probability of adverse actions in use compared to any other antibiotics.

Owing to the unique ability of bacteriophages to kill bacteria, bacteriophages have attracted attention as a potentially effective countermeasure against bacterial infections since their discovery, and there has been a lot of research related thereto.

Bacteriophages tend to be highly specific for bacteria. It has been shown that the attack of bacteriophage is specific, meaning that one species of bacteriophage targets only a single species of bacteria (or even a specific strain of one species). In addition, the antibacterial strength of bacteriophages may depend on the type of target bacterial strain. Therefore, it is necessary to collect many kinds of bacteriophages that are useful in order to get effective control of specific bacteria. Hence, in order to develop the effective bacteriophage utilization method in response to ETBF, many kinds of bacteriophages that exhibit antibacterial action against ETBF must be acquired. Furthermore, the resulting bacteriophages need to be screened as to whether or not they are superior to others from the aspect of antibacterial strength and spectrum.

SUMMARY OF THE INVENTION

Accordingly, the present invention has been made keeping in mind the problems encountered in the related art and is intended to solve such problems.

In one embodiment, a composition for preventing or treating an infection or disease caused by ETBF includes: a Siphoviridae bacteriophage having an ability to lyse the ETBF cells, and a pharmaceutically acceptable carrier.

In another embodiment, the Siphoviridae bacteriophage has a genome including a sequence as set forth in SEQ ID NO: 1; or a genome that has (1) a sequence having at least 93% query cover with at least 95% identity to SEQ ID NO: 1, (2) a circular genome topology, and (3) 69 open reading frames.

In another embodiment, the Siphoviridae bacteriophage has a concentration of $1\times10^1$ pfu/ml to $1\times10^{30}$ pfu/ml or $1\times10^1$ pfu/g to $1\times10^{30}$ pfu/g.

In another embodiment, the Siphoviridae bacteriophage has a concentration of $1\times10^4$ pfu/ml to $1\times10^{15}$ pfu/ml or $1\times10^4$ pfu/g to $1\times10^{15}$ pfu/g.

In another embodiment, the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, or mineral oil.

In another embodiment, the composition further includes one or more selected from the group consisting of a lubricant, a wetting agent, a sweetener, a flavor, an emulsifier, a suspending agent, and a preservative.

In another embodiment, the infection or disease caused by ETBF is acute and chronic intestinal disease, bacteremia, diarrhea, colitis, colonic neoplasia, or cancer. The cancer is colorectal cancer or colon cancer, but is not limited thereto.

In another embodiment, the composition is a solution, suspension, emulsion in oil, water-soluble medium, extract, powder, granule, tablet, or capsule.

In another embodiment, the composition further includes a second bacteriophage having an ability to lyse ETBF bacterial species, and the second bacteriophage has a genome that has a sequence having less than 93% query cover with at least 95% identity to SEQ ID NO: 1.

In another embodiment, the Siphoviridae bacteriophage has major structural proteins in the sizes of approximately 25 kDa, 48 kDa, 68 kDa, 75 kDa, 117 kDa, and 245 kDa.

In another embodiment, the Siphoviridae bacteriophage has a latent period of 10-100 minutes and a burst size of 1000-2100 PFU/infected cell.

In another embodiment, the latent period is 40-80 minutes and the burst size of 300-1500 PFU/infected cell.

In one embodiment, a method for preventing or treating an infection or disease caused by ETBF includes administering to a subject a Siphoviridae bacteriophage; and lysing the ETBF by the Siphoviridae bacteriophage.

In another embodiment, the Siphoviridae bacteriophage includes a sequence as set forth in SEQ ID NO: 1.

In another embodiment, the Siphoviridae bacteriophage has a concentration of $1\times10^1$ pfu/ml to $1\times10^{30}$ pfu/ml or $1\times10^1$ pfu/g to $1\times10^{30}$ pfu/g.

In another embodiment, the Siphoviridae bacteriophage has a concentration of $1\times10^4$ pfu/ml to $1\times10^{15}$ pfu/ml or $1\times10^4$ pfu/g to $1\times10^{15}$ pfu/g.

It is to be understood that both the foregoing general description and the following detailed description are exemplary and explanatory and are intended to provide further explanation of the invention as claimed.

Advantageous Effects of Invention

The compositions and methods for inhibiting the proliferation of ETBF, of the present application have high specificity against ETBF, compared with conventional compositions and methods based on antibiotics. The compositions can be used for preventing or treating ETBF infections without affecting other useful commensal bacteria and have fewer side effects. In general, when antibiotics are used, commensal bacteria are also damaged, thus entailing various side effects owing to the use thereof. Meanwhile, each antibacterial property of the bacteriophages such as antibacterial strength and spectrum (host range) are different in the case of bacteriophages exhibiting antibacterial activity against the same bacterial species and bacteriophages are usually effective only on some bacterial strains within the same bacterial species. Thus, the compositions and methods of the present application provide different effects in its industrial applications.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
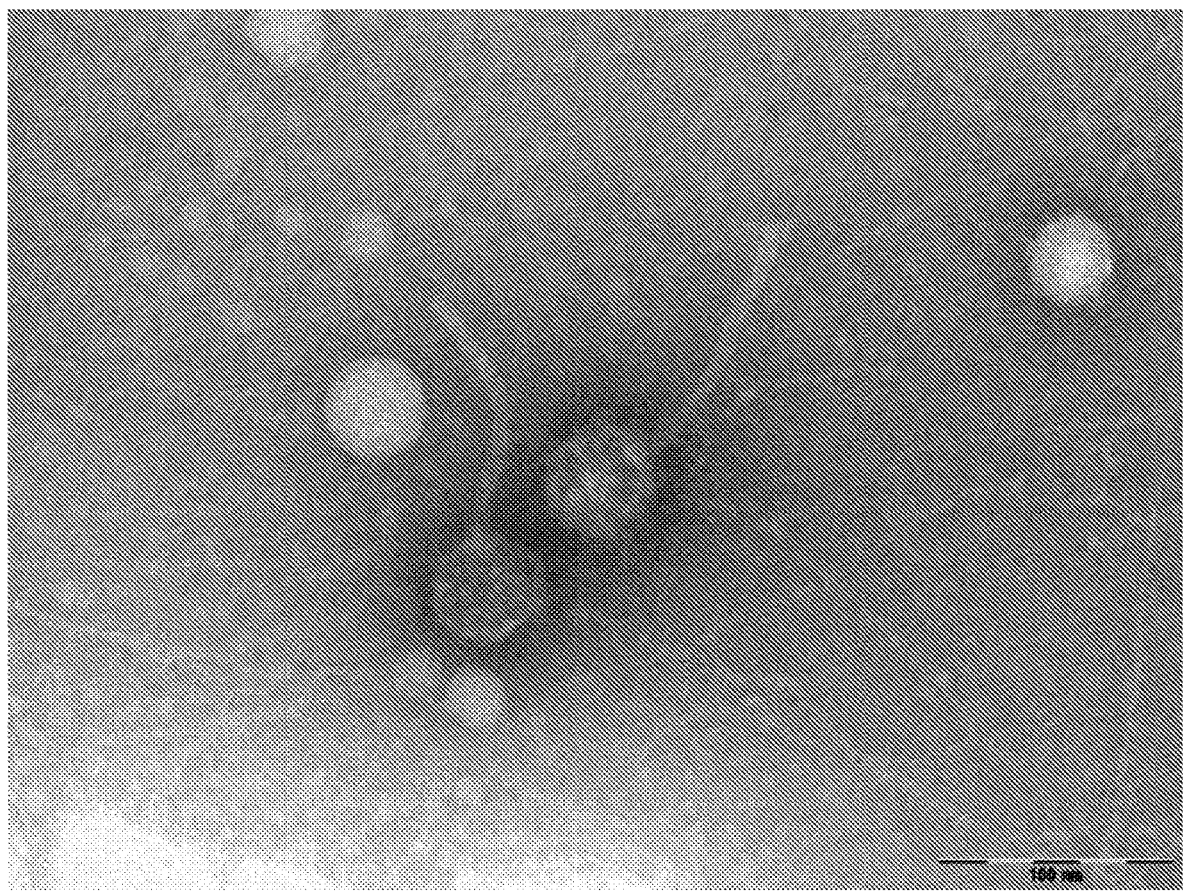
FIG. 1 is an electron micrograph showing the morphology of the bacteriophage Bac-FRP-3.

Reference will now be made in detail to embodiments of the present invention, example of which is illustrated in the accompanying drawings.

In accordance with one aspect of the present invention, the present invention provides a Siphoviridae bacteriophage, named as Bac-FRP-3, which has the ability to specifically kill ETBF and has a genome including a sequence as set forth in SEQ ID NO: 1. In some embodiment, the Siphoviridae bacteriophage contains a genome that has all the following characteristics: 1) including a sequence having at least 93% query cover with at least 95% identity to SEQ ID NO: 1, 2) having a circular genome topology, and 3) having 69 open reading frames; a genome that has all the following characteristics: 1) including a sequence having at least 94% query cover with at least 95% identity to SEQ ID NO: 1, 2) having the circular genome topology, and 3) having 69 open reading frames; a genome that has all the following characteristics: 1) including a sequence having at least 95% query cover with at least 95% identity to SEQ ID NO: 1, 2) having the circular genome topology, and 3) having 69 open reading frames; or a genome that has all the following characteristics: 1) including a sequence having at least 96% query cover with at least 95% identity to SEQ ID NO: 1, 2) having the circular genome topology, and 3) having 69 open reading frames.

The present invention also provides a method for preventing and treating infections or diseases caused by ETBF using a composition including the same as an active ingredient.

The bacteriophage Bac-FRP-3 was isolated by the present inventors and then deposited at Korea Collection for Type Cultures, Korea Research Institute of Bioscience and Biotechnology on Dec. 9, 2020 (Accession number: KCTC 14401BP).

The molecular weight of major structural proteins of the bacteriophage Bac-FRP-3 is approximately 25 kDa, 48 kDa, 68 kDa, 75 kDa, 117 kDa, and 245 kDa.

The latent period and burst size of the bacteriophage Bac-FRP-3 are 10-100 minutes and 1000-2100 PFU/infected cell, respectively, preferably 40-80 minutes and 300-1500 PFU/infected cell, respectively, but are not limited thereto.

Also, the present invention provides a composition applicable for the prevention or treatment of infections or diseases caused by ETBF, which include the bacteriophage Bac-FRP-3 as an active ingredient.

Because the bacteriophage Bac-FRP-3 included in the composition of the present invention kills ETBF effectively, it is considered effective in the prevention of ETBF infections or treatment of diseases caused by ETBF. Therefore, the composition of the present invention is capable of being utilized for the prevention and treatment of diseases caused by ETBF.

The diseases caused by ETBF in the present invention include acute and chronic intestinal disease, bacteremia, diarrhea, colitis, colonic neoplasia, or cancer, but are not limited thereto.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Bac-FRP-3 is included as an active ingredient. The bacteriophage Bac-FRP-3 is included at a concentration of $1\times10^1$ pfu/ml to $1\times10^{30}$ pfu/ml or $1\times10^1$ pfu/g to $1\times10^{30}$ pfu/g, and preferably at a concentration of $1\times10^4$ pfu/ml to $1\times10^{15}$ pfu/ml or $1\times10^4$ pfu/g to $1\times10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. Then, the formulation may be in the form of a solution, suspension, or emulsion in oil or a water-soluble medium, extract, powder, granule, tablet, or capsule. A dispersing agent or stabilizer may be additionally included.

In order to improve the effectiveness of above purpose, bacteriophages that have antibacterial activity against non-ETBF bacterial species may be further included in the composition of the present invention. In addition, other kinds of bacteriophages that have antibacterial activity against ETBF may be further included in the composition of the present invention. These bacteriophages may be additionally included so as to maximize antibacterial effects, because each antibacterial property of the bacteriophages such as antibacterial strength and spectrum (host range) are different in the case of bacteriophages exhibiting antibacterial activity against the same bacterial species.

In this description, the terms "prevention" and "prevent" indicate (i) to block ETBF infections; and (ii) to inhibit the progression of diseases caused by ETBF infections.

In this description, the terms "treatment" and "treat" indicate all actions that (i) suppress diseases caused by ETBF; and (ii) alleviate the pathological condition of the diseases caused by ETBF.

In this description, the terms "diseases caused by ETBF" and "ETBF infections" indicate acute and chronic intestinal disease, bacteremia, diarrhea, colitis, colonic neoplasia, or cancer, but are not limited thereto.

In this description, the term "Latent period" indicates the time taken by a bacteriophage particle to reproduce inside an infected host cell.

In this description, the term "Burst size" indicates the number of bacteriophages produced per infected bacterium.

In this description, the terms "isolate," "isolating," and "isolated" indicate actions which isolate bacteriophages from nature by applying diverse experimental techniques and which secure characteristics that can distinguish the target bacteriophage from others, and further include the action of proliferating the target bacteriophage using bioengineering techniques so that the target bacteriophage is industrially applicable.

In this description, the terms "query cover" and "identity" are related to BLAST (Basic Local Alignment Search Tool) which is an online search tool provided by NCBI (National Center for Biotechnology Information).

In this description, the query cover is a number that describes how much of the query sequence (i.e., the sequence of genome of bacteriophage Bac-FRP-3) is covered by the target sequence (i.e., the sequence of genome of the previously reported bacteriophage). If the target sequence in the database spans the whole query sequence, then the query cover is 100%. This tells us how long the sequences are, relative to each other.

In this description, the term "identity" or "sequence identity" was measured for "query cover," and is a number that describes how similar the query sequence (i.e., the sequence of genome of bacteriophage Bac-FRP-3) is to the target sequence (i.e., the sequence of genome of the previously reported bacteriophage). More specifically, the terms "identity" or "sequence identity" refers to the percentage of identical nucleotides in the spanned sequence part of the target sequence (i.e., the sequence of genome of the previously reported bacteriophage) or the query sequence (i.e., the sequence of genome of bacteriophage Bac-FRP-3) when the query sequence (i.e., the sequence of genome of bacteriophage Bac-FRP-3) and the target sequence (i.e., the sequence of genome of the previously reported bacteriophage) are analyzed by BLAST alignment analysis. The higher the percent identity is, the more significant the match is. From above definitions for "query cover" and "sequence identity", it will be obvious for the skilled one in the art that the differences of "query cover" and/or "sequence identity" between genomes of two similar bacteriophages make the differences of ORF (open reading frame)'s numbers arranged in the two genomes, then results in the discriminative characteristics (including the range of target strain and strength of antibacterial activity) of two similar bacteriophages.

In this description, the term "Second Bacteriophage" is any bacteriophage that has the ability to specifically kill ETBF and has a genome that has a sequence having less than 93% query cover with at least 95% identity to SEQ ID NO: 1 and has different characteristics from bacteriophage Bac-FRP-3 in terms of the genome topology and the number of ORFs, wherein the genome topology of the Second Bacteriophage is linear form.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing ETBF

Samples were collected from environmental or clinical samples to isolate the bacteriophage capable of killing ETBF. Here, the ETBF strains used for the bacteriophage isolation had been previously isolated and identified as ETBF by the present inventors.

The procedure for isolating the bacteriophage is described in detail hereinafter. The collected sample was added to a BHIB (Brain Heart Infusion Broth) culture medium (calf brain infusion from 200 g, 7.7 g/L; beef heart infusion from 250 g, 9.8 g/L; proteose peptone, 10 g/L; dextrose, 2 g/L; sodium chloride, 5 g/L; disodium phosphate, 2.5 g/L) inoculated with ETBF at a ratio of 1/100, followed by stationary culture at 37 C for two days under anaerobic condition. Upon completion of the culture, centrifugation was performed at 8,000 rpm for 20 minutes and a supernatant was recovered. The recovered supernatant was inoculated with ETBF at a ratio of 1/100, followed by stationary culture at 37 C for two days under anaerobic condition. When the sample contained the bacteriophage, the above procedure was repeated a total of 5 times in order to sufficiently increase the number (titer) of the bacteriophage. After repeating the procedure 5 times, the culture solution was subjected to centrifugation at 8,000 rpm for 20 minutes. After the centrifugation, the recovered supernatant was filtered using a 0.45 m filter. The obtained filtrate was used in a typical spot assay for examining whether or not a bacteriophage capable of killing ETBF was included therein.

The spot assay was performed as follows: BHIB culture medium was inoculated with ETBF at a ratio of 1/100, followed by stationary culture at 37° C. for two days under anaerobic condition. 2 ml ($OD_{600}$ of 1.5) of the culture solution of ETBF prepared above was spread on BHIA (calf brain infusion from 200 g, 7.7 g/L; beef heart infusion from 250 g, 9.8 g/L; proteose peptone, 10 g/L; dextrose, 2 g/L; sodium chloride, 5 g/L; disodium phosphate, 2.5 g/L; agar, 15 g/L) plate. The plate was left on a clean bench for about 30 minutes to dry the spread solution. After drying, 10 l of the prepared filtrate was spotted onto the plate culture medium on which ETBF was spread and then left to dry for about 30 minutes. After drying, the plate culture medium that was subjected to spotting was incubated at 37 C for two days under anaerobic condition, and then examined for the formation of clear zones at the positions where the filtrate was dropped. In the case of the filtrate generated a clear zone, it is judged that the bacteriophage capable of killing ETBF is included therein. Through the above examination, the filtrate containing the bacteriophage having the ability to kill ETBF could be obtained.

The pure bacteriophage was isolated from the filtrate confirmed above to have the bacteriophage capable of killing ETBF. A conventional plaque assay was used to isolate the pure bacteriophage. In detail, a plaque formed in the course of the plaque assay was recovered using a sterilized tip, which was then added to the culture solution of ETBF, followed by culturing at 37 C two days under anaerobic condition. After the culturing, centrifugation was performed at 8,000 rpm for 20 minutes to obtain a supernatant. The ETBF culture solution was added to the obtained supernatant at a volume ratio of 1/50, followed by culturing at 37 C for 2 days under anaerobic condition. In order to increase the number of bacteriophages, the above procedure was repeated at least 5 times. Then, centrifugation was performed at 8,000 rpm for 20 minutes in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, a solution containing the pure bacteriophage was obtained. The procedure for isolating the pure bacteriophage was generally repeated until the generated plaques became similar to each other in size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage isolated above was confirmed to belong to the Siphoviridae bacteriophage.

The solution containing the pure bacteriophage confirmed above was subjected to the following purification process. The ETBF culture solution was added to the solution containing the pure bacteriophage at a volume ratio of 1/50 based on the total volume of the bacteriophage solution, followed by further culturing for two days under anaerobic condition. After the culturing, centrifugation was performed at 8,000 rpm for 20 minutes to obtain a supernatant. This procedure was repeated a total of 5 times in order to obtain a solution containing sufficient numbers of the bacteriophage. The supernatant obtained from the final centrifugation was filtered using a 0.45 m filter, followed by a conventional polyethylene glycol (PEG) precipitation process. Specifically, PEG and NaCl were added to 100 ml of the filtrate until reaching 10% PEG 8000/0.5 M NaCl, and then left at 4 C for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% gelatin, pH 8.0). The resulting material was referred to as a bacteriophage suspension or bacteriophage solution.

As a result, the pure bacteriophage purified above was collected, was named the bacteriophage Bac-FRP-3, and then deposited at Korea Collection for Type Culture, Korea Research Institute of Bioscience and Biotechnology on Dec. 9, 2020 (Accession number: KCTC 14401BP).

Example 2: Separation and Sequence Analysis of Genome of Bacteriophage Bac-FRP-3

The genome of the bacteriophage Bac-FRP-3 was separated as follows. The genome was separated from the bacteriophage suspension obtained using the same method as in Example 1. First, in order to remove DNA and RNA of ETBF included in the suspension, 200 U of each of DNase I and RNase A was added to 10 ml of the bacteriophage suspension and then left at 37 C for 30 minutes. After being left for 30 minutes, in order to stop the DNase I and RNase A activity, 500 1 of 0.5 M ethylenediaminetetraacetic acid (EDTA) was added thereto and then left for 10 minutes. In addition, the resulting mixture was further left at 65 C for 10 minutes, and 100 1 of proteinase K (20 mg/ml) was then added thereto so as to break the outer wall of the bacteriophage, followed by reaction at 37 C for 20 minutes. After that, 500 1 of 10% sodium dodecyl sulfate (SDS) was added thereto, followed by reaction at 65 C for 1 hour. After reaction for 1 hour, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes in order to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 1 of water. This procedure was repeated to obtain a sufficient amount of the genome of the bacteriophage Bac-FRP-3.

Information on the sequence of the genome of the bacteriophage Bac-FRP-3 obtained above was secured by performing next-generation sequencing analysis using Illumina Mi-Seq equipment from the National Instrumentation Center for Environmental Management, Seoul National University. The finally analyzed genome of the bacteriophage Bac-FRP-3 had a size of 45,462 bp, and the sequence of whole genome was expressed by SEQ ID NO: 1.

The homology (similarity) of the bacteriophage Bac-FRP-3 genomic sequence obtained above with previously reported bacteriophage genomic sequences was investigated using BLAST investigation, the genomic sequence of the bacteriophage Bac-FRP-3 was found to have a relatively high homology with the sequence of the *Bacteroides* bacteriophage vB_BfrS_23 (Genbank Accession No. MT630433.1) (query cover: 93%, sequence identity: 96.63%). In addition, the number of open reading frames (ORFs) on the bacteriophage Bac-FRP-3 genome is 69, whereas *Bacteroides* bacteriophage vB_BfrS_23 has 72 open reading frames.

Based upon this result, it is concluded that the bacteriophage Bac-FRP-3 must be a novel bacteriophage different from conventionally reported bacteriophages. Further, since the antibacterial strength and spectrum of bacteriophages typically depend on the type of bacteriophage, it is considered that the bacteriophage Bac-FRP-3 can provide antibacterial activity different from that of any other bacteriophages reported previously.

Example 3: Analysis of the Major Structural Proteins of Bacteriophage Bac-FRP-3

Figure 2:
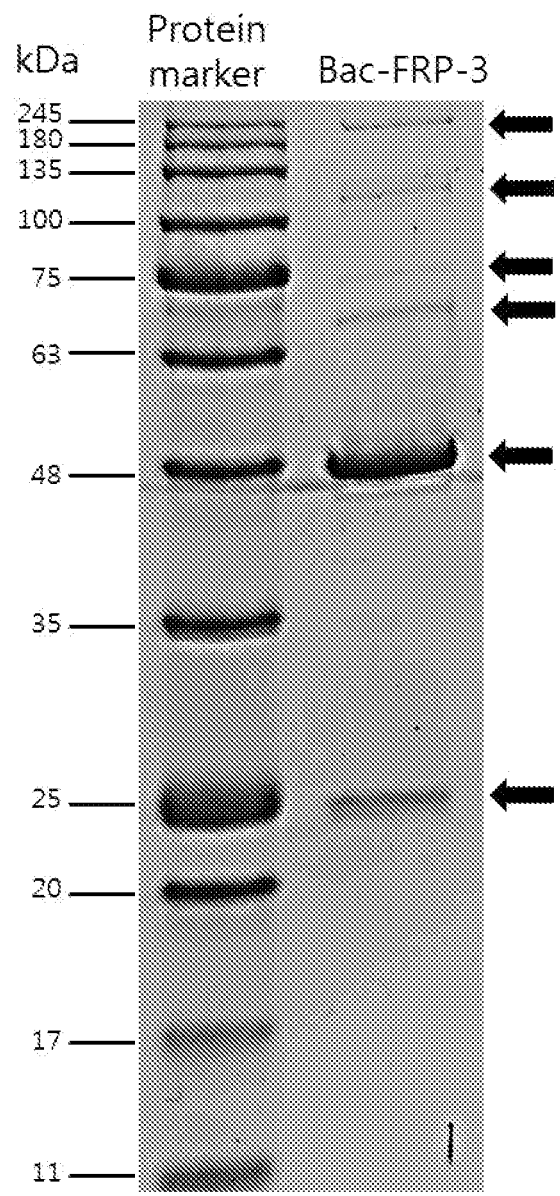
FIG. 2 is a result of the analysis for major structural proteins of bacteriophage Bac-FRP-3.

One-dimensional electrophoresis was performed to analyze the major structural proteins of the bacteriophage Bac-FRP-3. To obtain the proteins constituting the outer wall of the bacteriophage Bac-FRP-3, 200 μl of the bacteriophage suspension prepared in Example 1 was mixed with 800 μl of acetone, which was vortexed vigorously. The mixture stood at −20 C for 10 minutes. Centrifugation was performed at 13,000 rpm at 4 C for 20 minutes to eliminate supernatant, followed by air drying. The precipitate was resuspended in 50 μl of electrophoresis sample buffer (5×), which was then boiled for 5 minutes. The prepared sample was analyzed by one-dimensional electrophoresis. As a result, as shown in FIG. 2, the major structural proteins in the sizes of approximately 25 kDa, 48 kDa, 68 kDa, 75 kDa, 117 kDa, and 245 kDa were confirmed.

Example 4: Investigation of Ability of Bacteriophage Bac-FRP-3 to Kill ETBF

Figure 3:
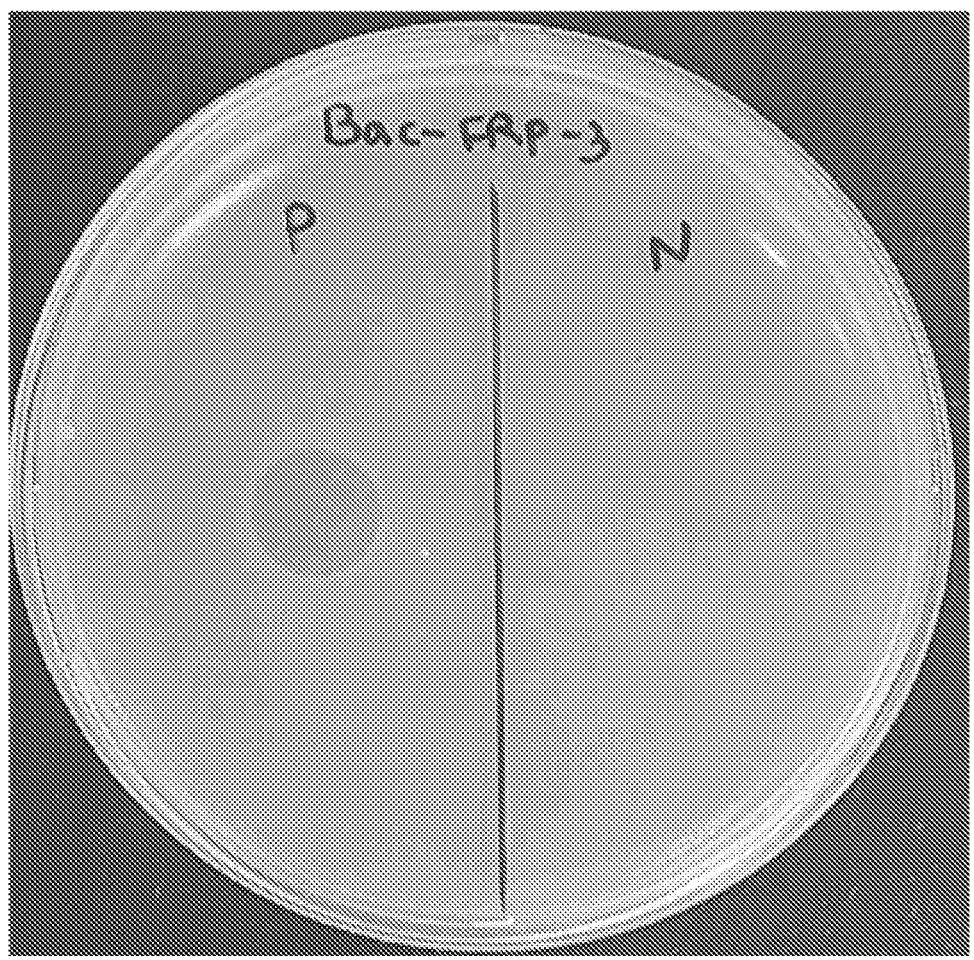
FIG. 3 is a photograph showing the results of an experiment on the ability of the bacteriophage Bac-FRP-3 to kill ETBF. The clear zone is a plaque formed by lysis of the target bacteria.

The ability of bacteriophage Bac-FRP-3 to kill ETBF was investigated. In order to investigate the killing ability, the formation of clear zones was observed using the spot assay in the same manner as described in Example 1. A total of 5 strains that had been identified as ETBF strains were used as ETBF for the investigation of killing ability. The bacteriophage Bac-FRP-3 had the ability to lyse and kill a total of 3 strains among 5 strains of ETBF as the experimental target. The experimental result thereof is presented in Table 1 and the representative result is shown in FIG. 3.

TABLE 1

Test of antibacterial activity of bacteriophage Bac-FRP-3

| Tested ETBF strain | Test result |
|---|---|
| *Bacteroides fragilis* CCARM 18104 | + |
| *Bacteroides fragilis* CCARM 18105 | − |
| *Bacteroides fragilis* CCARM 18106 | − |
| *Bacteroides fragilis* CCARM 18107 | + |
| *Bacteroides fragilis* CCARM 18108 | + |

* +: clear lytic activity, −: no lytic activity;
CCARM: Culture Collection of Antimicrobial Resistant Microbes (Seoul, Korea)

Meanwhile, the ability of the bacteriophage Bac-FRP-3 to kill *Bordetella bronchiseptica, Enterococcus faecalis, Enterococcus faecium, Staphylococcus aureus, Streptococcus pneumonia, E. coli* and *Pseudomonas aeruginosa* was also investigated in a separate experiment. As a result, the bacteriophage Bac-FRP-3 did not have the ability to kill these bacteria.

Therefore, it is confirmed that the bacteriophage Bac-FRP-3 has strong ability to kill ETBF and a broad antibacterial spectrum against ETBF, suggesting that the bacteriophage Bac-FRP-3 can be used as an active ingredient of the composition for preventing and treating ETBF infections.

Example 5: Growth Characteristic of Bacteriophage Bac-FRP-3

Figure 4:
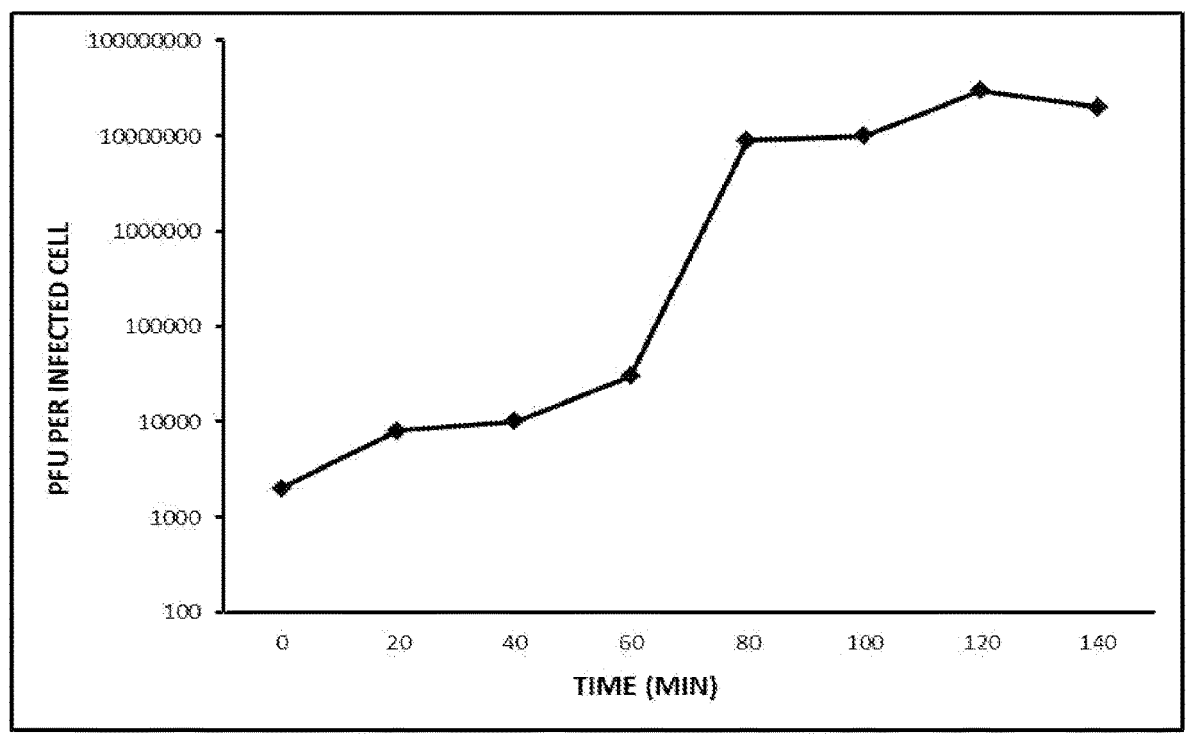
FIG. 4 is the one-step growth curve of bacteriophage Bac-FRP-3.

The growth characteristics of bacteriophage Bac-FRP-3 was analyzed by one-step growth curve analysis. One-step growth curve analysis of bacteriophage Bac-FRP-3 was performed as follows: 50 ml of BHIB (Brain heart infusion broth, Difco) culture medium was inoculated with ETBF at a ratio of 1/100 and followed by stationary culture until exponential phase ($OD_{600}$=0.4~0.5) under anaerobic condition. Upon completion of the culture, centrifugation was performed at 8,000 rpm for 5 min and a bacterial cell pellet was recovered. The recovered pellet was suspended in 50 ml of BHIB. The resulting material may be referred to as a bacterial suspension. The bacteriophage Bac-FRP-3 was mixed with the bacterial suspension at a multiplicity of infection (MOI) of 0.1 and incubated at room temperature for 10 min, and then centrifuged at 12,000 rpm for 30 seconds. After supernatants were removed, the pellets containing bacteriophage-infected bacterial cells were suspended in 50 ml of BHIB and incubated at 37 C without shaking. Aliquots were taken at 20 min intervals for 140 min, and the titers in the aliquots were immediately determined by the conventional plaque assay (FIG. 4).

The latent period of bacteriophage Bac-FRP-3 was estimated to be approximately 60±10 min with average burst size of about 1100±500 pfu/infected cell.

Example 6: Experimental Example Regarding Prevention of ETBF Infection Using Bacteriophage Bac-FRP-3

100 l of a bacteriophage Bac-FRP-3 suspension ($1 \times 10^8$ pfu/ml) was added to a tube containing 9 ml of a BHIB culture medium. To another tube containing 9 ml of a BHIB culture medium, only the same amount of BHIB culture medium was further added. A culture solution of ETBF strain (CCARM 18104) was then added to each tube so that absorbance reached about 0.5 at 600 nm. After ETBF was added, the tubes were transferred to an incubator at 37 C, followed by stationary culture, during which the growth of ETBF was observed. As presented in Table 2, it was observed that the growth of ETBF was inhibited in the tube to which the bacteriophage Bac-FRP-3 suspension was added, while the growth of ETBF was not inhibited in the tube to which the bacteriophage suspension was not added.

TABLE 2

Test for bacterial growth inhibition of bacteriophage Bac-FRP-3

| | $OD_{600}$ | | |
|---|---|---|---|
| Classification | 0 minutes after initiation of cultivation | 120 minutes after initiation of cultivation | 240 minutes after initiation of cultivation |
| Bacteriophage suspension was not added | 0.5 | 0.6 | 0.7 |
| Bacteriophage suspension was added | 0.5 | 0.4 | 0.3 |

The above results indicate that the bacteriophage Bac-FRP-3 of the present invention not only inhibits the growth of ETBF but also has the ability to kill ETBF. Therefore, it is concluded that the bacteriophage Bac-FRP-3 can be used as an active ingredient of the composition for preventing the ETBF infections.

Example 7: Preventive Effect of Bacteriophage Bac-FRP-3 on the Infections of ETBF in Animal Model Preventive effect of the bacteriophage Bac-FRP-3 on weaning pigs affected by ETBF was investigated. 4 weaning pigs at 25 days of age were grouped together; total 2 groups of pigs were raised in each pig pen (1.1 m×1.0 m). Heating system was furnished and the surrounding environment was controlled. The temperature and the humidity of the pig pen were controlled consistently and the floor was cleaned every day. From the 1$^{st}$ day of the experiment, pigs of the experimental group (adding the bacteriophage) were fed with feeds adding the bacteriophage Bac-FRP-3 at $1 \times 10^8$ pfu/g according to the conventional feed supply procedure, while pigs of the control group (without adding the bacteriophage) were fed with the same feed without adding the bacteriophage Bac-FRP-3 according to the conventional procedure. From the 7$^{th}$ day of the experiment, the feeds of both groups were contaminated with $1 \times 10^8$ cfu/g of ETBF for 2 days and thereafter provided twice a day respectively for the experimental and the control groups so as to bring about the infections of ETBF. The administered ETBF suspension was prepared as follows: ETBF strain (CCARM 18107) was anaerobically cultured at 37 C for two days using a BHIB culture medium, after which the bacteria were isolated and adjusted to $10^9$ CFU/ml using physiological saline (pH 7.2). From the next day after providing contaminated feeds for 2 days (the 9$^{th}$ day of the experiment), pigs of the experimental group (adding the bacteriophage) were fed again with the feeds adding the bacteriophage Bac-FRP-3 at $1 \times 10^8$ pfu/g without contaminating ETBF according to the conventional feed supply procedure as before, while pigs of the control group (without adding the bacteriophage) were fed with the same feed without adding the bacteriophage according to the conventional procedure. From the 9$^{th}$ day of the experiment, diarrhea was examined in all test animals on a daily basis. The extent of diarrhea was determined by measuring according to a diarrhea index. The diarrhea index was measured using a commonly used Fecal Consistency (FC) score (normal: 0, soft stool: 1, loose diarrhea: 2, severe diarrhea: 3). The results are shown in Table 3.

TABLE 3

| | Fecal Consistency score | | | | | |
|---|---|---|---|---|---|---|
| | D9 | D10 | D11 | D12 | D13 | D14 |
| Control group (bacteriophage suspension was not administered) | 2.5 | 2.25 | 2.0 | 2.0 | 1.5 | 1.0 |
| Experimental group (bacteriophage suspension was administered) | 1.25 | 0.75 | 0.5 | 0.25 | 0 | 0 |

From the above results, it is confirmed that the bacteriophage Bac-FRP-3 of the present invention could be very effective to suppress the infections of ETBF.

Example 8: Example of Treatment of Infectious Diseases of ETBF Using Bacteriophage Bac-FRP-3

The therapeutic effect of the bacteriophage Bac-FRP-3 on diseases caused by ETBF was evaluated as follows: 40 of 8-week-old mice were divided into a total of 2 groups of 20 mice per group, after which subgroups of 5 mice each were separately reared in individual experimental mouse cages, and the experiment was performed for 7 days. On the second day of the experiment, 0.1 ml of an ETBF suspension was administered to all mice through intraperitoneal injection. The administered ETBF suspension was prepared as follows: ETBF strain (CCARM 18107) was anaerobically cultured at 37 C for two days using a BHIB culture medium, after which the bacteria were isolated and adjusted to $10^9$ CFU/ml using physiological saline (pH 7.2). At 2 hr after administration of ETBF, $10^9$ pfu of bacteriophage Bac-FRP-3 was administered through intraperitoneal injection to mice in the experimental group (administered with the bacteriophage suspension). 0.1 ml of saline was administered through intraperitoneal injection to mice in the control group (not administered with the bacteriophage suspension). Both the control and experimental groups were equally fed with feed and drinking water. Whether or not the mice survived was observed daily starting from the administration of ETBF until the end of the test. The results are shown in Table 4 below.

TABLE 4

Survival rate

| | Survival rate (%) | | | | | |
|---|---|---|---|---|---|---|
| | D2 | D3 | D4 | D5 | D6 | D7 |
| Control group (not administered with bacteriophage suspension) | 100 | 75 | 60 | 35 | 15 | 15 |
| Experimental group (administered with bacteriophage suspension through intraperitoneal injection) | 100 | 85 | 85 | 80 | 75 | 75 |

As is apparent from the above results, it can be concluded that the bacteriophage Bac-FRP-3 of the present invention is very effective in the treatment of diseases caused by ETBF.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Accession Number

Name of Depositary Authority: Korean Collection for Type Cultures (KCTC), Korea Research Institute of Bioscience and Biotechnology, 181 Ipsin-gil. Jeongeup-si, Jeollabuk-do 56212, Republic of Korea
Accession number: KCTC 14401BP
Accession date: Dec. 9, 2020

What is claimed is:

1. A method for preventing or treating an infection or disease caused by enterotoxigenic *Bacteroides fragilis* comprising:
   administering to a subject a composition containing Siphoviridae bacteriophage Bac-FRP-3 and a pharmaceutically acceptable carrier,
   wherein the Siphoviridae bacteriophage Bac-FRP-3 is deposited in the Korean Collection for Type Culture (KCTC) under accession number KCTC 14401BP and has an ability to lyse the enterotoxigenic *Bacteroides fragilis* cells and the genome sequence as set forth in SEQ ID NO: 1,
   wherein the Siphoviridae bacteriophage Bac-FRP-3 has a latent period of 10-100 minutes and a burst size of 1000-2100 plaque-forming units (PFU)/infected cell,
   wherein the Siphoviridae bacteriophage Bac-FRP-3 has structural proteins in the size of approximately 25 kDa, 48 kDa, 68 kDa, 75 kDa, 117 kDa, and 245 kDa; and
   wherein the composition has a concentration of Siphoviridae bacteriophage Bac-FRP-3 of $1 \times 10^4$ pfu/ml to $1 \times 10^{15}$ pfu/ml or $1 \times 10^4$ pfu/g to $1 \times 10^{15}$ pfu/g.

2. The method of claim 1, wherein the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, methylcellulose, methylhydroxybenzoate, propylhydroxybenzoate, talc, magnesium stearate, or mineral oil.

3. The method of claim 1, wherein the composition further contains one or more selected from the group consisting of a lubricant, a wetting agent, a sweetener, a flavor, an emulsifier, a suspending agent, and a preservative.

4. The method of claim 1, wherein the infection or disease is acute or chronic intestinal disease, selected from the group consisting of diarrhea, colitis and colonic neoplasia, bacteremia, and colorectal cancer.

5. The method of claim 1, wherein the composition is a solution, suspension, emulsion in oil, water-soluble medium, extract, powder, granule, tablet, or capsule.

* * * * *

SEQUENCE LISTING

```
Sequence total quantity: 1
SEQ ID NO: 1              moltype = DNA   length = 45462
FEATURE                   Location/Qualifiers
misc_feature              1..45462
                          note = Siphoviridae bacteriophage
source                    1..45462
                          mol_type = other DNA
                          organism = Unidentified
SEQUENCE: 1
ataataaccc ttcgttcggc tatttggtta tattaccgaa aagcgcagag gaaacaattg   60
tttcgactaa aataacgcct tcgaatgatg atgcagcgta tttctatttc tataaaaccc  120
cacagaaaga aacaacccaa acgtatgtaa aatgggctgt aattactgag ggtgatattg  180
gtgtagccgc atggataccg tcacgaactg aggctaaaac aggcattagg aacttatttc  240
caatatcacg gatgcagaca gcgactaaca atcatttgaa ctattttgat attacaggat  300
gggtagcaac tgtatacagt gaagaagaat ttaagtcaag gtttaaacca tctacgaaat  360
ataccataac agggaaatat actattcttg gaaagccaac atcaggaacc ggatacaaag  420
atagtatcgt agcttttgt atgtggaata actctaattt aatagacctt tggcgtaaaa   480
ttgtcgagta tgaagcagta ggagcttcgg gagaaatatc taatacattt actacacctt  540
cgaatctcga tgggtatagg atagtagtgt ataccatgta caatacagga aatttaggag  600
agtttcgttt tactgatttg atggtatcag aaggaattga ggcagtaggg tggacacaag  660
caccggaaga tatagaatac gactaccgga agtacaccga tacgcagata ctggctgttg  720
atgggaaaat cgaactatct gtgaatacgc aattgaacaa gcgtgtaatt ggtgggtcaa  780
accttctttt aaaatcggat atttgtgttt ccgaggctac tgcacccaaa tcaattatca  840
tgtctaagta ttggagggaa cttgctggaa aaaaaatatc tatttcattt gattatgaat  900
atagtaatct tgttttaggg ggatcgcaaa gaataggact cgaagctgcc atcttaaaag  960
atggtacttc acagtatcac tatatcggag cttttaagaa ttttgattca acttctttaa 1020
aagctgattc gggaaggttt gccaataccg tgacagttcc taatgatata ttaaattctg 1080
aaagcatatc tattaatgtc tacattcaag ttgggagcgg gtctaaagtg aagatgtgta 1140
actttcagat tgaaataggt gacacagcaa ccggatggaa acccgcaccc gaagatagcg 1200
taaatgagtc aaaagagtat acgagacagc aaataagcat tgttgagggt aaaatcacca 1260
ctacggtaga aaagataaca gaggttgacg ggaaggttac cggacttgct tcacgggtag 1320
accaaaccga aaagagtata acgtctgttg ttggggatat taatgttctt aatagcacta 1380
caaatagacg cattactaag caaatagatt taacaggatg ggacaataat aagtttttcc 1440
ctctcactat aaatctccct gtttactaca aaactaaggt tgttataagc cgtccttaa  1500
atacagcata cggaaaacct tcatacagta cacatgatac cggtttttct atgaacttaa  1560
cgtttgagat gtccggttcg ggatgggggt ctttgcctga cgtaacaaat atatttgatt  1620
atacacgtgc gtggagtaca ggaccgatag ttgtagattt gggacaaata agagaaacct  1680
ctacttgcgt aatgggtatt cgtggtgggt ctaagtatga tgtaaccgtt tacgacacaa  1740
caaactccga tgtgataaac gtttatcaaa cagattatca cggttcgtac ggtacatctt  1800
tccccgtacg caccgatggt acagagccat tccggacgta tggttactac tctgagataa  1860
aacagacaca agaaagtctc tcagcaacgg ttgcaaaggt agacgatcaa ggcaggcggt  1920
taagtgcggc tgagttaaca ttatctgccg atcacgcaaa attatcggtg gtagaaacga  1980
ctgcaaacaa tgccaattca cttgccggaa ctgccaacaa caaagcggaa gcggcagacg  2040
gtcgagttac cgccacacag aacggtttgg tcgagactgg aataaacatc acgtcccgca  2100
aaatcgtgtt aaagtctgat aacgtccttt tccaaaacaa cgcaggacag cagacagccg  2160
ccatcaatgc gaacggaaaa cttactgcaa acgcaattga agttggtgag gttgttgccg  2220
gaggttttgc ggcacagcgc atcactaccg gaaacctgac tgtaacggat ggtgcggtta  2280
ttggggggaat gactatcaca gggggagtgt tgaccggaaa gaacatcaat atacaggatg  2340
gtgcaaagat cggtaacttc accattgtat cgggtatatt ttccgcccaa aatacgcccg  2400
caggcataca aatgactcta tcgaataatg ccgctacttt tgacagtagc ggagtacgtg  2460
tagaacataa ttcgggtggt tatgcgttga ctactacggg taacggaaga gtattcctaa  2520
```

```
cagggtcaaa ttttttgggtt cagtgtaagg acgttgattt tatgggtgct caaacatgga  2580
aagccccggg tgttttttac gcatgtacga ttttggcaaa cggagcaatc ggtaaaacat  2640
gggggaaccc tgactttcac ataacaagag taactaaaaa ctcaacaggg agatatactg  2700
ttaatactac cggttccaat ggggactact ttgttatgat tacagcgtat gacccttcaa  2760
actgctaag tacaacagta gaaccatact cagagggaca gtttacgtac aaagtattcg  2820
atgtaaatta tagcatgcgt gacgqcgag ttattattta ttttttgtgc atggttaggt  2880
agtttagtgt tttaattaac ggtaagttgg ttttatcctt cttaccgttt acctttgtac  2940
caaacattaa tcaattaata taaaattatg gaaaagaaaa gtttagattt tgatttaaag  3000
tcagtagttt acacgaaaga dacaaaagtg atggactacc attttgagac ggaaaacggt  3060
aagtacgtag gtcaattaac cacggtatcg acagagccgg ataagtacaa cattactcac  3120
tgtacggctg atgtgtcaga gaaacaaatg gtagagatgc ctgatacttc cggtagtcct  3180
attctgcaag agcaatatgt tccggtcgga tcgcttgcca tccgtgacgg tcgctttgag  3240
gcaaaccagt ttcctctatc tactaaaaca tccgtctatg tgaacgactt tcaaaacttc  3300
atatttgcgt taaccgcacc taaagcagta gaataatgaa tgttacacaa gaacagttaa  3360
ggttaatgct tgtatcggca attagtccga tacttgcgtt tctcacccct acgagcggtt  3420
ttataaccgc ccttgtgttc atgttcggct ttaacattat ttgcggtatg cgtgccgatg  3480
gggtcaattt gtcggtaaat ggtgttcgta ggttcactat gctaaaattc atctcagccg  3540
tgcaggaact tattttgtac atccttgtga taaccgttat cttttcgtct gtggcgaaga  3600
tgggggatca cgatgcagca gttctatcgg caaagacgat tacatacgtc ttcatgtacg  3660
tatatttgtc gaacggtttt aagaaccttt gtataagcta tccggataac aaatctttcc  3720
ggttaatata ccatattgtc cggtttgagt ttaagaggtt gatgggagag aacgcagcaa  3780
agatagtcga ggaacacgaa gaaaaaattg agattgaaac taagtaatta acacgggagg  3840
tttaacgcct cccttttaaac tttatcaaaa tgaatatatt cacattaaaa gagctaaac  3900
gctcagcaac ggcagaggca aaaggcattg ataacgcgcc cacaccggag gttgaaaaga  3960
acttaacgtt gttagtagat aacgtactgg ataaattacg tgagatttac ggtaaaccga  4020
tcacggttaa ttcgggctat cggtgtccgg agttaaacaa agctgttgga ggctctaaga  4080
catccgatca cgtgaaaggt tttgcggctg atattaccgg aggcagcaag gaagagaacg  4140
aacgccttt caatatcatt aagcacaatt tccatttcaa acaattaata gacgagagag  4200
atttttcatg ggtgcatgtc tcctacgatc cctctaatct caaaaaccaa atactaaagc  4260
tatgaaaaag caattatttg cgttttttagc gacttttgtt cttttgccttg gcattgtgtc  4320
gctattactg ataaacgctg atttacggaa gaaaaaaggct attgcagaaa gaaatgttag  4380
cgtcctaaca actcagaacg ttgcgtaccg gacgaaaagt gggcaaagtg tcatgaaggc  4440
agaggaattg aatctgactt taaatcatta ccggaacacc atacaaggga aggataacac  4500
tataagagag ctaaagcagt ctattaagga cttgaaaagt cacacaagcg ttcaaacatc  4560
aactgagacg cattttagaa cgccagtacg ggatagtgtt gttcttcgtg atagtttggt  4620
tatcgacaca atgaaatgcg taaatatgcg atctaaatgg cttgacttat ccggctgcat  4680
agatagcaac ggcacgtttg ccggaacaac cgttacccgt gatagcttgg aaatattaaa  4740
catagagcat agaaagcggt ttttgtggtt tcgactaaaa aaggtgaagt ataggggagtt  4800
tatcgtaacg agcaaaaacc cacatacaga gataacaggt tttaacgtaa ctacgataat  4860
aaagtgataa ttccatgtta aaacagttaa tgcacgttaa agtatttgct actgagaaat  4920
atatccgtat atttgcagcg tagaagttat tactaacgtc attaacagcg gttattgatt  4980
ttcatagaat catgttttta gaagatttgt atcacatttt atcttaaact gtcggtatgc  5040
gaatatagac agtttttaat tagaacattt tcactaacta tatatattgg gttttgtcat  5100
aattacattt ttccccctcc gcttgtgaaa gtagagggg ttttttattac cttatccgaa  5160
cacgcctcaa aagttaaatt agtgttaaat attaaactta tgctttgata tttaaaatat  5220
ctccttaact ttgcaacgtc aaaaggaaac gaattactaa caataaaact tatagttatg  5280
gaagaaaagg aatttatta ttgcttgacc ggagagatta acgtattagg aactgtcaag  5340
gctaagacaa taaaaagtgc tatgaaactt gtagcggcta ttcagagagg tgctatattg  5400
aatgatccgg aaaggaaatc aatctttttgg agcgtttcac gtgctgatct cccgtttaaa  5460
cttggtcgta ttgtatacac aatatgctat tcagatgggc ctatttgttc acatgtatgc  5520
taacaataaa aatttagagt tatggaatta gagaggcaaa gagtataatg  5580
gaagaaaaag cttttttgca aaaaaagctt gaaaggcttc agtccggctg tcttagtaga  5640
acagaattat atttcagttc gggaaaatatc gtaacatttt cggaaggtga tggcgaattt  5700
tatgaaggtt tgcgcaaaaa ctttgaaaag tctataagag aatatattga aaatcgtatt  5760
ggctacttg aatctaaatt tgataaacta tgatacgatc gtttaataag tcgggttcaa  5820
catctatgct gacagataag gaaaaagcgt ttaaccgcta ctgcctaact aacaaggaag  5880
tttcatataa cttaatgcgt atagaaatgg cagttgttca aatgtcgtat tacggcaacc  5940
gttcatcgga cgttacgcta acaaccgata gttctgaggt tttgaatgct atttatatag  6000
tcctaacaaa cgaagggttt aaatattcct tcaatttacc taataaagta ttaaccataa  6060
gtatttttta atttaaaatt taatcaaaat gaaagaagaa gtaaaattgt tcagagcgtt  6120
aatcattgtt tttgtgttac ttgtgttcac cttcgtgtta acttcgtgcg gtgatgatag  6180
tgacaatgtg tatcaaacag aatattctat tgatgttccg gcatggcaga cggtttatgt  6240
taatggtgag gttacaacgt ctatatctcc atatgtttgg gaacatgtgg acttatcaga  6300
caaatgtgtt agagtattct cagcagggca tgttagttat cacaaggtta caagaccgtc  6360
acacgatgat ttaggcttta ccgtttattc aatagaaggt agcaataacg aaaggtttgc  6420
atacaataaa aataaaggta tattgcaata ttggtgcaca agaaacggta ttgaaacagt  6480
tgttgtttat cgtgaattaa agtaagtttc atttacccct caccccggtgg cggttaaccg  6540
ggttattaag tatgaaagta aatgttgtat tagaagagaa aaagattcca tgtttcgaag  6600
ctaaatacgg tttagtgta tataacgata aaggacaaaa atatactatc gagttcgata  6660
taatgggaaa tttagtagtt agtagtccaa aaggtacgtt attagtaaaa cccgaatgta  6720
acaacaaaat atcaattaga attgaatgat atgaaagaga taaacgaaac tcaattacag  6780
ctatctactg agggaaaaag acttcccgat atgataaagc aggcgaacgg catacacgaa  6840
cttgttaagc agaaactttc tgagtataac tcaatagagt ataccgatga taatataaag  6900
gtggcaaaag ccgatagagc cactttaaac aaggcgaaaa agggacttaa cgacagccgt  6960
atagaacttg aaaaggcttg gatgaaacca ttcaacgaac taaggatgt tgttaacgaa  7020
acttgtaagc tgatcggtga agcttcttca cgaatagata gtaagataaa ggaaacggag  7080
gaaaggggaga agcaaaagaa actggatcaa ataagggagt atttcgagga acacaatgaa  7140
aatcttatct tgtttgattt tgctttccgt ccggagtggc ttaataagac taaagcactt  7200
tcagttgtga aaatggagat agacgaattg ttcaaaacag tagacgatga tcttaacaga  7260
```

```
ctgaaagagc attttgcggg agaggcgttt tatattccgg ttatcgacaa atatacgtct    7320
acactcgact acaacaaatc attcgactat ggaaaccacc taaaagaagc tgtaatacaa    7380
gccgcaaaca gacagtttga acagaaggcg acagataaca cgcttcagca acaaaagcca    7440
gaaattaagc ctcaaaacga gccaaagact aacgaagaag aagtttatat acgaggcttt    7500
aaagtccatg taacgagaaa gcaggctttt gcgcttgctg agtttatgaa tagccacaat    7560
ataaagtttg aaagcatatc aatatagacg gtagcccaat tgggctacct tttttttgttt   7620
tgtttgcaat ggttaatcta ttgttaaaac ttaaagtttc acttgaactt ttaaataatg    7680
tgcttatatt tgcagtgtcg aaagaaacaa agtagtaaca attaaaaatt agaattatgg    7740
aaaatgttag attaacaaaa aagcaaaaag gagataaatt taagagtgaa cagttggtga    7800
aagcactcga aaagagattc aaaggtaata ttaacaataa tttattttaa aatggaacag    7860
tatttagact tactaaaaga gactttaaat tatggtgaaa agagatcaga ccgaaccgga    7920
acgggaacta tcagtttatt cggcttgcaa cgatcttacg atctgcgtga cggtttccca    7980
cttgtcacaa ctaagaaggt attcacgaag ggaattatac atgaactcct ttggatgtgt    8040
aaaggtgata ccaatataaa ataccttaaat gaaaatggtg ttcatatttg ggacgattgg    8100
gcaaagccct ccggtgatct tggacgcata tacggtaaac aatggcgtga ctggcgtata    8160
aatagcaaaa tgaaagtaga tcaaattgat tcagttatag atatgattaa gtttaacccg    8220
gagtcaagaa ggctaattgt tagtgcttgg aatgttggag aaatacacat gatggcaatt    8280
cctccgtgtc actgcttttt tcagttctat gtgtctgagt ccggttattt ggacttgaaa    8340
ctgtaccaaa gaagcgcaga cctatttta ggcgttcctt tcaatattgc atcttattct    8400
atcttgctgt ctatgctgc acaggtttgc ggtttaaagc ctcgtagatt cattcatacg    8460
atcggggacg gacatatata tttgaatcac gttgaacagg tgaaagaaca attgagtaga    8520
gagccgttcg cccttcccaa attggaatta aacccgaata ttcgtaatat attcgatttt    8580
aagtatgaag atattaagat agtaaattat aactgccatc cggctataaa gggagaggtt    8640
gcggtatgaa tgaaaaagaa ttttacaggt ttttagccta taataaattg gtagattttg    8700
aaagatacct tcacatggaa tctgtatatt atctgaataa cttgctaaag aaaaccgtta    8760
attcgtattt gagagattgt atattgaacg ctataaatca taaattagcg ggattataat    8820
ttaaaaggga tgtgcaacgc tttgccatcc ctttttagtt tctatatatc acataccgaa    8880
actatcgttg ctctatgaaa caaatctaac aatatgtagt aacaagtatg aaagtgatac    8940
aaaggtaggc ttttgatact atccaatggt taaaacgagt ctttttatat ttcattaaca    9000
ataaaattaa agaattcctt tgcatattta aagtttatcc ttaactttgc gacatcaaaa    9060
aataagtagt aacattaaaa acgaataata tgcagattaa aaaagatcga aattacaaat    9120
tgcttgtgca ggtttgcaag aataaaggta ttccattctc ctacgaaaaa cttgttttgt    9180
ttttgaataa gtacatttat gaagatgaag aagattcagt atttggatat acaatatctg    9240
atattgattt ttcaatcgct aaacatatat cggttgatat ttgcggaatg cttacattaa    9300
gcaatattat cagtaaatta acttgtatcg gtgcgggaga ttgcccgaat tgccggaggtt   9360
tactcagatt gatagaatct tatcccaaat ttagcaaaca gtattgcgat cgtgattgtg    9420
agccggagag agaggaagaa aatgtatatg aatgtttaac atgtgaaag gaggttgttt     9480
tatgaatatt gaaaacacaa tgatccgtat caatgatgcg attataagcg cacgtatgaa    9540
cggcaaaaag attacgaaaa aggatattgc agcgttgttg tggaaggatt caaagcaaag    9600
aacgcaggcg gtaaacatgt ctgccttgtg taaccacaaa acccaaacga taaaaataga    9660
gtgggtgaaa gagatatgcg aggctaccgg agtcgatgcg aatttcctat ttaatattaa    9720
ccctaaaaaa taaaagttat gattaaaaat ttacccaaca ttcaaaacga aatgaatgtt    9780
caaaagtcga gatttaacaa ttttggcgga tacaaataccc gttcgtgtga ggatattttg    9840
caagaagcga aaagggtgtg cgaaaaatac ggatgttatg ttatggtgac tgattctatc    9900
gaatttatcg aaggcgtttt ttacgtgaag gcaaccgcaa agattgttga gactgaaacc    9960
gggtttattg aaacatgttc ggcttttgca cgtgaagaag atagcaaaaa ggggatggac    10020
ttagcacaat taaccgggc tacatccagt tatgcacgaa aatacgcctt atgtgggctt     10080
tttgcaaatag atgatagcat agacagtgat tcaatgaacg gagagccgga gacgaaagaa    10140
aaacggcaaa agacagcctc aaaacaagct gccaacacaa gtaataccgg aagtaactct    10200
aattatttgg gtgtgctgat tgatgaaata aagaaagcaa caactatata acatttgggt    10260
gatattcaca agaacaacgg tcaatttcat caaaacgatg agttcatgaa cgctttagta    10320
gttagaaagg cggaacttga aaaggcggaa gcagaagcaa agaaggtata ataattcgg      10380
gggatgcgtt ccccccaataa aaacaaaaga aatatgaaag aattaacatt actccccaaa    10440
ttggttaatg ccgatgtaac gtatatcagc gagacacatg aatattttc aagagattt       10500
agaaaactga gaggaataac aggttttatc aacgatcaat tattccggg aaaacttgat      10560
aatataccgg ataatatttt gagatcggca actgagagag ggaaagcggt tcacgatgaa    10620
gtagagagaa tcgacaaaga aggtattgag ccggaaacgg tttacggaga gaactatttg    10680
gatttaaaag ccgaaagcgg tttaattcat atcgcatctg agtatattct aactgataac    10740
gagtttatcg cctcaccgac cgataaagtg tatttaggta gctctgaaaa ttcagtcgta    10800
ttgggtgacg ttaaaactac ctataaactt gatttgcttt atctgtcttg gcagcatca     10860
atatacgcct acctttcga gagacaaaac ccaaacttga agtagaggg acttatcgca       10920
atttggctga gaggtgacaa ggataaggac ggcatttct ccgttgaacg cataccggac       10980
agcgaaatag aattgttcct taattgctgt aagaatggcg ttcgatatgc agataatgca    11040
agcaaagata gctacatagc aaaaattggaa tcactgcccg caaaagttgc gcatatcgaa    11100
gaaggcgttt acgaacttct tgaaatgcaa aagaagatag acgagcattt aggcaagttt    11160
aaagaacagt tgttaggtct gatgtctgag gcgaaagctg acaatataaa aggggaactt    11220
atttcagtca caagaaagaa agcgtatagc cgtgaatcac ttgattctaa agcactgaaa    11280
gagcaatacc ccgaaaatata cgatcagttc gttaaaacat caaatgtcaa agaatcaatt    11340
caattaaaag cgttgtaata actaagtaga aaggagctaa aaagatgata ctaactactg    11400
gtaagatatt atttgttact gattcagatg attctgactg ccatattgag aacttgagga    11460
cggagtataa aacaaatatt tattgcataa agattgataa aacgcttaaa cctccctatt    11520
accagctatt ccatgagtgt aaggaggca acgaaaatt gcatcgtgaa ttattctct       11580
ccagcaaact ggaaaagatt gtaaaatata taagtgaaaa tattcaatag aaagaagaaa    11640
gaaaattgtt tgatttttgtt gtatgtggga atagctacat aactaaatgt ccattctcgc    11700
aaaagaaggt tggttcaaaa ccttgttatg attgcaaata ctttgttagg gaaaaatcat    11760
acatagatat tggaagcggt ggcgaaggtg ttattatatg ttctaaactg aataagaaat    11820
gaataaaatt aaagaatcag aattaaatac cctcttagaa aatggtgatc tttgtgatta    11880
ttgtccgaat gttagaggcg aaatatctaa agggcttttat gatttgtgcg aagggtgcta    11940
ttgcgaacag gcaaaggata attatgtact tgaaaacgat ttagattatg aagaggaatg    12000
```

```
aatttattaa taagcttatt aggcgttcta attatatgga taaacttgta tatgtaacgg  12060
cagacggagg aagaagggaa ataataaagt taaagccgaa aaaaaagaaa tattataatt  12120
ccctcgaata ttatagagat attaaaagga cgtctaatat aaacatttat tttgagatat  12180
ggtaacaata tctgagagtt tagcgaacga gatcggttta gagggtgcga ctgtgtacag  12240
ctatgtatct atcatcctat caacggactt ttataaggag cgttttaagg aatgccggct  12300
taaaggcaag aagtatacag ccttcatatc aataagcaag ttgaaagaga taattccctt  12360
cctatcgaca aagaagctgt ataacgctat gaacttgtta gtagaaacag gatacctaaa  12420
agagctacca ttacgaaagc cgggtttaaa tacaacccga tgttaccaac ttgttaatgt  12480
gatccaacat tgcgagtagc ctataataca cccaccaacg ttttttagtt gtgtgggtgt  12540
tttttgtaca gcacgattct gtgcaatctg tatataccta attatcagat atttgaaaaa  12600
caaataatgt taaatcataa aaaatagatg ttttttccatt gcagtatata ataataaacg  12660
ctatatttgc agagtaaaat ttaaaacagt atgtatatga aagtagaaaa cttagttaag  12720
attaagagtt atgccgattt aaagggagtt acagtacctt ggatatggag gcttattaag  12780
aggggaaaat tagagtatat tcaaattgat ggtgcatgct tcattgagtt aacggatgaa  12840
gaactgaaaa agtatgcgga gtacaaagaa cggataagtc cattttttgaa tagcaaatag  12900
tattaatcat taaaattta gaaaatgaaa gatttagttt ttaagggaga atcaaatcaa  12960
gttttaacaa gcagcttatt ggtagctgat aagttcggga aaaatcatag agatgtgtta  13020
gaatctatta gagagctagt taagggtaga gcggaaaatt ccgctgtact aaaaatgttt  13080
gttccatcta cttatatagc gtctaacaat aaagaaaacc cgatgttcat aatgaataga  13140
gacggtttta cattgttggc gatgggcttt acaggagaaa aggcatttca atttaaattg  13200
gagtacatta acgcctttaa taaatggag gaaactatta agaacggagg ttttaacgtg  13260
cctaaatcgt tccgtgaagc attattgctt gcagcagaac gcaagaagt tatagagaat  13320
cagcaaaagc agatcgaaga aaaaacgca aagatcgaag ctgacaagcc gaaagttttg  13380
ttcagtgaag cggtctccgc ctcaagcaaa tctatcttag tgcgtgaact tgcaaaactt  13440
atcacccaaa acgttatca gatcgggaa aagcggctat acgagcgatt gagaaaatcc  13500
ggatacccttt gcagcgttgg agaatcacgc aatcaaccta cacagacaca catgaatatc  13560
ggtttgtttg agattaagaa gcgtgttatt atggacggtg atgaagcaaa ggtttacaat  13620
acaactgtcg ttacgccaaa aggagtacat tatttcatta ataagttttt agggagggga  13680
atgaaatgac gcattgtttt gacgataaag tagcaacaaa gttaggagtt gaagcggcat  13740
gcgtattgca caacttcgct ttttggataa acaagaatat agccgataac cacaattatt  13800
ttgagggcag atattggact tataacacaa gggaagcgtt atctaaacta ttcccgtata  13860
tgagtcaatc taagatatat agagtgtatg aaagttggga ggaagaagc tatttgttga  13920
aggggaattt taataaatcg ggtatagata gaacaacgtg gtacgcatta acagataagt  13980
gtataaaatt cctttttgag tgcggatata cgcttatagg ctattctgag ccgattttgc  14040
aaaattgcaa aatgcaagtt gcagaaatga acaatgcaag ttgcagaaat gaacaaacaa  14100
taccagatag tatatataca gatagtaata ctaaatctcc taacggagat tatagtatag  14160
ccacgcgcga agaatctgtt ttgttccgg ttgaaaagaa accttagcc tcagagatat  14220
ttggctttac tgcaaaaacc ttagatgtga ctaagaaagt gatagagcga acagatagtt  14280
ttttcgatca gctaacattc ccgttcgagt cggaaggaaa gtaaaaagcc tttttatgtgc  14340
taatgactca accaaagtgg cgggtaaaga ctaagactct aacagctatg caagcaaacc  14400
taaacgagat tgcgcaattt gaagaagtt ttgctatgct attgataaat cagagcatat  14460
ctaagggatg ggcttcactg gtatacgagt caacgccaaa ccagtatatg caatggctac  14520
gggaaaagac gggagtctcc ggaaatacac agccggcaaa caatactaaa tcgtattttc  14580
agagtgacga acagcgcagg atgtatcagt cttatttaac ggatgacttt atatagcatt  14640
ttaaggctta aatttcaatt ttaatcacta agacaataaa agtatcatgt atttggagaa  14700
aatagaaaat tcgggcggaa aattagcaaa atacgaaggt tgcggatcgt ttatagaaa  14760
gaaccgataa ttttatgaaa gtggcaactt cggacagcta tcaaaagtag atcaaaagat  14820
attccgtgat tcaactttgc ttttggtgtc cgaatgtaca gacgaaagaa aaagaataga  14880
taatttttct aaggttctta acggagtatg tttagagact ggtttaaaaa tgccggatgt  14940
ccgggacgca ggaagtatat tttatgctgt ttgtgatgtg atagatatgt attttgatga  15000
tctatcgttc aatgaaattc gttttggcatg gcgttactt gctgtcgggg aactcgaccc  15060
gttttttgcca aaagacagat acggtagtcc ggacaaaaat cactatggct ctctttcggt  15120
tgattatatt tcaaaggttc taaagcgta taagaaacga aaggttgaaa cgatggaacg  15180
agtttctcag attatgccgg atgaaaagcc aaagccgaca cctgaacagg aaaagatgtt  15240
tttaaatttg caggcataca attttgttct cgccccttttg aagtataagt attcgggacg  15300
tttccgcata gagcgtgaca ggataataaa cgagtctaca tttgcgtaca tggaacgatt  15360
gggatatgat atgtcgtat tacctacgtt agctgacaag aaagaagctt tgtttcaatt  15420
tcaaggtaga cccgtaaaca gctttgcgca aattttcgaa aaagagtgta tttcgaggtt  15480
tgggatagac cacgaagcag tttattttcg tgcgtactg atagccaaga aagaaagtt  15540
attccagtat tgggatgaaa tgttagcctt ctcaaatgaa ggtgatagat cagaagataa  15600
tatttggaag ttgtattact acattcaata aaaccaaaag ttatgaatag aagaaaagta  15660
aaaaagaacg gttatcggat aaggcttaca aagccttccg ataaattcgt ttatgtctct  15720
gactcgttaa catacgaaag gagaaaaaag gagggaaaga gatgttatac tctgtattgc  15780
aaatatgcgt ctattaacta tttgtgtgtt tctcgaaatc agcaaaatc tttaatgaaa  15840
gggttcttgt tactatggga atagatatta tttgcgcaat agacccgggt gtgtcggctg  15900
gtggaatagt ggtatataag ccgggtaata gtcttattac tatcccaatg ccacgcacgg  15960
caaagggtat ttttaacgtg tttcaaaaag tgaagcgttc cggtagccct gcaatattca  16020
ttgagcgtct ttccggttcgt ggggtgact ccggaggcgg gaaagaattt agaatagcaa  16080
ctatgttgga gaattataac taccttgtat gttgtgcgct cgttcttgat attcctttgt  16140
tcctatgtgc gcctatttcg tggcaaagtg gtttaaatc gagggagaaa ggagagaaag  16200
aggaaaagaa ggatagaaaa gaaaaatatc tgaattatgc gatgaagcaa ttcccacttg  16260
caaacgtgaa attgtggaat agtgacgcta tatgtatttt gcgtttcgca caaatgaaga  16320
tgatttgcga tgtagattgg ttttcaagta acatgcagaa cgaaacagc acggaaatat  16380
tccttcttta cattttctta ccctctgttg gacgatagta ttaaatcgta gggttcaata  16440
gaaaacgagc taaaaacga tctaattgaa tcggtgaaag aattgagaag cgcacagaag  16500
cgatttgagc gattcgggga gagatacaga gagggaaag aaaagcgga aagaaagta  16560
gatgaaattc tgtcggttat cgaagataag caactatcta ttttctaaca aaagttaaat  16620
aacgggtatt tcggaaagat ttaccgtttt ttatttgcgt gaatttaaag ttttgcttta  16680
atttgcagcg tagaaataaa aacagtagta acaataaaat caattaatta tgcaggaaat  16740
```

```
taacaagaaa ttaagtgaac tgtcagtaga aaaggttttg gatagaccgg agtatagaaa   16800
agagctttct atttattggg agggcttaaa agagcaacgg gaaaaggtat ctttccaaat   16860
attgaataat ggcggtatcc ctaaaaggat aataatagac agagttggga aaatggatgc   16920
agaacaactt gtatcagaat ttaaactgat acttgacaga aagagtgagt tgcctgcaag   16980
tctgaggcac tttatttcgg atgtatgcgg aaaggtattt attagttggt ttacaaaagt   17040
gatcgaagat gaagcaaaag aaaataacga taccogggaa ggtaactaag gacggtaagt   17100
tatccatcta catgggcgag cttaacgagt ttatgaagaa caacgcaggg aaaaatatta   17160
ttgcggagtt tacggtatta gaaccgtctg attcttcata cttgcgtgga tactactttta   17220
aatacgttgt tccccaattt cagaaaggga tgtgcgaaaa tgggtacagg tggagcgaag   17280
aagaaacgga ggcttatatg cgtagtattt gccctattac gatgcggtgaa gttgtagatg   17340
ttgaaactgg tgagtataga aaggactcag ttaaagttac cgatttaagc aatagcgaat   17400
ttgtcgaata catagaattt ttaaaagcagt ttgcggcaga agaatttagt atttatattg   17460
aagaaccaaa tagatttgta agatgaaaga aaatgaagaa atgactttag aggaaaagtt   17520
caatttgatg tgcgaagcat taagcatatc tccggaagaa attatcac gggatattac   17580
acgttatgta tcacttcgaa gaaattgcat tatccatcag ctttacgcct ataaaaatca   17640
cggtttaccc gaattgatag gtcgcacgaa ggttttaatt atgaaagcgc atgaatgttt   17700
tcaaggcgaa ttagatgtga aagatatgac agccgtagag ttttgtacggc ttatagacga   17760
acgactgcaa aagtatattg atggcaaaga agattaagaa tcttgttctt gttcattgca   17820
cggagtgtag gttcagttca gatcaccaca atttgatttg ttattgcagt aagtttaaaa   17880
agaagttatg cagttgccct aacattggga gggtatgcga gttttacatt aaaaaataaa   17940
gtatcatgtt aaaagaaaat tttgaattaa agagagttaa attttttgaat aacggtttag   18000
aggtagatta caatgattgc cgtttggttg atggtgagaa aacaaagacg tttcacaagg   18060
taaaatgccc cgaatatccg catagagatt taagaattgc ggcaaatgag cttcgttcat   18120
acatagttga attgatggga ataatgaatt ttaggaacat cacctatttg tctgatttgg   18180
caaaacaaga caatgagtta agtagacaat tcgatgaata ttttgaaacg cttgcaaccc   18240
gtatacgat tagtgagata gtctatgatt ccgaaaagaa cacaatagtt ttcaaatata   18300
ttttcacggg agtagatttg tcccggttga aaatgcaaac gagcaaaatt atgttgtacg   18360
gtgaggggtt gaaatttgaa atagcactac aagaagattt taaagcactg aaagatgaaa   18420
ttttcaagta tctttttgag aataagcgtg cacaattgga gctattcggt gagacagcaa   18480
cggcagaacc ggacgatagt ttgacgccag atgatgattt agaaggtgac gatacgtttt   18540
ttgatgatga agaagcagag cagccggagt tgatcgaaga agatgtacac gattgatacg   18600
tttgaggaaa tagattattg tttaagcagg gggtataacc cctgctatt taataataat   18660
ttcgatattg aacctaaaac aaggtatgaa atatttaaaac ggatgttcgg ggagggtcac   18720
ggacagaggg aaaatgaacg tttcttccgg tatatgtggg atattaagcc tcactattgt   18780
gaagaatgtt taaagccgtt gactggatac tcagccgttt atattagcca tattataacg   18840
aggggatcga acccaatgat tgcgcacgat cctcgtaata taaacatact ttgtttcaat   18900
tgccacaatc gttgggaaca cgccaatacc cgcaaggggga tgcggatata tcaaagtaat   18960
ttagaaaaaa taaaagttct taaaagggac agtttaaaac tgcaaagaa atgaaattgg   19020
taaaatttga acttgtatcg ggaaatgaaa ttatgattaa ccctaaatct gtggaatcaa   19080
tagttaaata tacagatgat tcggtgtata ttaacacagt aggtgcagat atgccgtata   19140
tagttaaagg ttcaattgaa gatgtcaata aagtactaag cgaaggtagc aatattgatt   19200
caatagccgg acttatggtt atcgtctttta ttggaattta catattatca acattaacaa   19260
atttattatc gtaatgaact taaacaaaat cgaattgatc gggcgtgttt gcgctgatcc   19320
gcaagtaaaa accttcgata acggaggggaa agtatgtaat cttttctatcg caacgaacga   19380
aagggcatat aaaacgagta acgggatcga agttccggaa aaaacagact ttcataatgt   19440
aacattcaaa ggtaaattgg ctgagatttg cgggcagtat gttaccaaag gaatggagtt   19500
atacgtagag ggtagtttac actatcgtaa atatacagac tctaataacg ttgaaagaac   19560
tatttctgag atcgttgtaa ggtctatgca gatgggaaga aaagcggggtg agggaaacca   19620
gccggcagcc ggaggcaacg gaaaccaaca gccgccaacc ggatgttata gctgtcaaca   19680
gcaaccgcct cagcagatgt ttacacaaaa tgatgatttg ccgttttaag gtaattctaa   19740
attgggggatg tatattgcat ccccttttttt gtgttaaata catgttaaaa cttaaactttt   19800
agattgcaat attaaatatt atccttatat ttgcagtgtc aaaaggaaac aaattactaa   19860
catttaaaaa taaatattat ggcaacaatg acatcaaaac aattttgtga gagaatgtat   19920
ggaatgtata acttgcttgg cggtggtgat ttcgatgtg ctcactgttc agacaatagg   19980
ttttcttgcg gatatagaaa ggagaatacg gttttaacaa atgcacttat gaaggcgtgc   20040
gataatcaca aagttcctta taagataaaa gcaaacaaat attgtatcaa tttcgtagta   20100
gaattttaaat aataatagcg gtagaaatac cgctttaaaac ttatagttat ggaaaaagaa   20160
agattgtccg gtcaatacaa aatagcgatg tgcaaaaata gaggaaacga tacatttgcc   20220
ggaactgttg ggataagaac aggttttatg tatcagtgcg gtgcgtatca gtattttact   20280
tattgggaga atgacaataa aatatcggtt actgaatcaa gtacaggttt tcgtgtaatg   20340
tctttggatg ttgaaaaggg agaaactcct aaaactgcgc atgataggt agttgataag   20400
ttgaagggtt ttgatccatc tttagcaaac tggaatagtg ctaaagagat gatgaagaaa   20460
tataatattc catatcctct taatgaatgg atagtagggc taaaagacat aaaccatgaa   20520
tgaagaagta gaaaaagcaa gatcggtgag taacgaagtt atttcggaaa ctatcagaaa   20580
atcgactgat aatataaagg caatggagga cgatttcaga ttagtaagaa agaagttgcg   20640
gaaaattggc gatcgaataa aatttgagag aagaaacttt gatatataca acgaagaaat   20700
aaaaaggagg gttaagtatg gaatttggta acttactgtt agatagattg gggttcaacc   20760
gtgaaatgtt ggagataaa cttttcagaaa tatccgctaa ggagaaagaa ataagagttc   20820
taaagaaaga agtttccggt ataatgggaac acatatcaaa attggaaagt acgttaaatc   20880
atggagagca ttattattgc ggtgcttgct gctatcttga aagtaaatgt aataagggaa   20940
aatataagtg tcttgaaaca ggagaataca agaaatacca ctgtaaggcg tgtgagaaat   21000
ttagagattt accattttaa taactaatta taaattaaat attatgattg atttttaatca   21060
aaaagtatc tctttaacta aagagtgtac agaacaacat gaaagaatga aggcaaaagg   21120
ttttatgac tcagaggttt ttgagtgtaa aaaatggggcg ttgatagtgt ctgagttctg   21180
cgaagctatg gaggcggaaa gaaaaggtag agttataaga aacgatgtgt atgactttgt   21240
tctgaatagg caatcaaatg aaggttttga gcagtgttt aaggaaaggg taaggatac   21300
agttagcgat gaactcgcag acgtgtttat ccggtgtatg gacgcaatag gacattctat   21360
tgataaaatt gcgtgtcctt ccgaaatttt tgttttttcaa agtatggtta gcgatcattt   21420
caataggtta ttgtatcttg aaaaatctat ttcatcaatt gtttattatg ccattcaatt   21480
```

```
tgtaccgaaa tctgtatttg gcaaatcgtg cattaccgag tatactaaca tgatggcaat   21540
aaccattgca gccgcaaagc tttataacat agacctatct aaagcaatag aggcaaagat   21600
aagatataac gagttgagag gtcaaaaaca tgggaaacaa tattaattca attgatatgg   21660
aagaaaaaat tattgattta gtaagaagaa gcgtttatta tggtgatccg gaaggttacc   21720
aagttggggg gtgccattac aaggcacccg gcatgcaact ttctgagttt ttagaaagga   21780
ataaagttgg tttcttggag gggaacgtaa tgaaatatgt gtttaggcac gataagaaga   21840
acaaagaaga agatttgcta aaggctatac agtatatcca gttattcta aagtacagat   21900
atggaaaata cttggtaggt gatacgctgt ttagtgagga agaatataaa aaggcgattg   21960
aacttattga aaaacaagat acgattgaac ttgatactac cttatccga aatgcgttga   22020
aaacccaaac aattgtttcg cctaaaatat cggtagacaa ggcaacttta tatgttgcaa   22080
agctaagaga ggttaaagcc gaatatatcg aaagttttga tttgaaagat ataaataaat   22140
gcaggctttt agatatgggg ttgttatttt gtggtaaaga taagttttt gtttattttg   22200
agtctaaaaa cagacaaacc atagttgtta agcccgggga ttatattgta ctgaaagatg   22260
atgggatata tgaaacgtat tcaaaacaag aatttgaatc tatatttcag ccaaaatact   22320
aacaaaaatc aataacaata ggtcacgttg caaatatagc agcgtgactt tatttttata   22380
ttatctataa tagtgttatt tttgcgcata ttgaaagatt atataatttg tagtacaata   22440
tacagaatag aaattataac ttaaaaatac gtcttaaaat ggataaaaaa ataggttcaa   22500
tgaaaagagg gcagggaagg catagccgga gacgaaca gactgaaaga gaccgttcct   22560
ttgcctctga tttgttttg aaaggttatt cttatagaag aatagcggaa gcgattaacg   22620
agcgaaataa ggcggatgaa ttgccgtata ccgtgactta tcaaacgtg tataatgata   22680
ttcagttttg cctgactcag tggaaaagag aacagttcga taatatagat cagtatatta   22740
cgcaggaact ccaatctttg gataatgtag ctcgtgaacg tgtgggaagg tgggaaaagt   22800
ctaagcgtcc caaatgtaag acaaagtata ttttagggaa ggctaaggag gtgcaaaagt   22860
aaacaacaac gggtgatcct tctttttga atgtagttct caacgtgcag caaagaaaag   22920
caaggttgtt ggggtatgac tcaccgttat gtataaactt ggtgggagat aaagaaaagg   22980
aaaaacccaa atacgatttt tcggatgtcc cggaggacgt tttagaacaa ttggcggatt   23040
ctttgcaaaa tacgcgagggt aaaaagtgaa aaaagtaaat gaaataccac cggttgagat   23100
tgtgaagtat gttgcgagga agaagtttaa gaactatgcc aaattcatag atgataaaat   23160
agttctgagt cagtttcaca aaacttacta cgagattctc gataggtttg cacatggtaa   23220
gatcaaaaaa ttgattgtta ccgttccgcc tcaaactgga aaatcagagg gtagcagtag   23280
aaagctacct tctttcctt tggggcttaa cccgtctta aagatattga tcggttctta   23340
tgccgcatca ctcgcagagg ggtttaataa ggatgtacaa agaatcatgg atacacctga   23400
gtataaaagc ctattccccg acacccggat aatgggagag gaaaaaaaa cgaggtatca   23460
agcgttttgcg agaaattcaa aaatgactga aacaatccgga aagggtgggt atattatatc   23520
cgttggtcgt aatggtagtt tgactggtaa atctgttgat atagccattt tggacgactt   23580
atacaaggac catatggagg caaattctcc gattatccgg gaagctgctt ggaaatggta   23640
caccaccgtt gtaaccaccc gtctacacaa taacagtcaa cagcttattg tatttacgag   23700
atggcacaag gatgatttaa taggtaggat cgaagataaa gagaatgtta tcaatgttga   23760
aaagtgggaa gatttggata gtataccgga aggtgcgtgg gttaaagtaa acttccagc   23820
tttaaaggtg ggagaaccaa cagagattga tccacgtttg cctggtgaag acttttggga   23880
agaaaaacat agcgctaaga aattgaacgc acaagggaa cttgatagaa atgaatttga   23940
atgtttgaac caaggaaacc cgggtagcgc tgagggtatt ctatacgta actttaaaac   24000
gtcaccgat aaaaacgatt ttggtgtgtt ggtcggaagg ggtaactaca ggactgtgc   24060
agatacaggt agtgactacc tttgttcaat ttgctatgat aagtatcaat caaaagaagc   24120
ggtttggaat gaaaaggaaa gaaggtataa gcatcttgtt ttctgccttg taacggacgt   24180
tatttatacg actgagccaa tagaggtcac gcaagtaagt gttcccgata tgctaaatag   24240
aaatgataca gattatgcaa atatagaaag caataacgga ggacgctctt tcgctgttaa   24300
tataagcccc aaaacaaaga ctgaaataaa ttggttctgt cagaagttaa ataaagaggc   24360
tcgtatattg tcgaacgctg caaacgttac tcagtctatt gtaatgccgt acgggtggga   24420
gtcacgtttc ccaaaattcc atgaacatgt aacaaattac cttcgtgaat ttcagcgaa   24480
caagcacgat gatgcggcag atgttttaac tggcatagtc gagaaagaag ttattccaac   24540
tatatatcaa aaaagaagag gaataagggt tataaactga taaagtagga aaatgtatca   24600
gactttcaag tttatacggt atattgcaa agtaaaatca attgtttaac taaatttta   24660
taattatgtt gtattgtgat tgtcctttag gagcagcact tccggatatt cccgcattta   24720
gctgtcccga caatttcggg caagttcaaa aacttgcttt tcagagactc gaaaaaacgg   24780
caggaactgc aaatactatg actgccgaaa gtatcgcaaa gttggctaca tggactcccc   24840
tactgtcagc aaaagacggt actaagtag tagttacgcc ttatatttac gagccgacag   24900
tagaggcgg cgctgccctt acttatgag gtggaaacgc aactcccgga ggtattgtag   24960
aaattttggg gtcggagtcg acaccgttta cggcttcgtt caagaagttg ccgcaaacca   25020
ttatcaaagc tatgaaagcg ttgatgtgtg aagcgggtca aatcggtgt ttccttatca   25080
acggtaacgg acaaattgct tgcgataaga cgggtgataa tttgcacggt ttcccggttt   25140
ggtcgctgtt tatcggtgat aagactatcg gaggtttgga agcgccggat agcaatgcta   25200
ttacgtggaa cttcatgcct aattggtcgg acaacttcac tatcgtgaaa cctgagttta   25260
accctctgac tcagttagtt cctttctgcg gtgtaggcgg atgatagcta aaaaacgta   25320
tatttccctc agttgtgaag aactgggga aactcgttta ttcgatattg aacacgctga   25380
gagactttg ggaatggtta ataatggagg gtggcatata ccgggagact cagaatttaa   25440
attaaatgaa aatgggaaaa tcattagacg aaataaggga gatatacaga catccggagg   25500
ggataagtca gatagcgaaa gcgaaggaac acgaaagaaag aatagcgttt cacacacggg   25560
taagaacgga cgatgatcgc aataagccag taattgcatt tcttctctaag gttaagacta   25620
ggatagcgaa agacaaatat gatattttcc tatctatgtt ccatttcccg gttaaaacaa   25680
atggtgttac ttctgagata ttcgacaaac tgagccgtgt tttcgatggt aggaatccgg   25740
tttataacta tcagtttaaa tcatcagagg atcgtgacga ctgggagtat taccggacgg   25800
atgtttttaaa agaaccttcg gtttggagta cggacggttg ggataatttc aagcatagaa   25860
ttaactcgt tttggtcgtt gatatgccgg aggtacaggt aggaaaaag ccagagcctt   25920
atttttttg gttgcctatc gcaaacgtcc tttcttatcg cacatgtggg aaagactgta   25980
atttgatggc ttatatcatg tacgtaacgg acgaaaacaa gatcgtatac attgatgaag   26040
aacgctatgt gagatttgat aagacgaggg agaacgactt gattttagag gtagataata   26100
tgcacgattt gggatattgt ccggctcgtt tcttttggtc tgactctatt tcattgagtg   26160
aacccgacat taaaataagc cctataacga gcgaactcga ctctttcgac tggtatcttt   26220
```

```
attattctac tgcaaagaag catttagatt tatacgcatc ttatccgatt tattccggtt   26280
atgaacgtga ttgtcactat gagtcacacg atggcaaaga acggtgtgat gatggttttt   26340
taaagaacga aaaaaacgag tggataacag gagcggacgg aaaaccgatg gcgtgcccga   26400
tttgctcaag caagcggttg aggggcgcag gctcttatgt tgagatacccatcccggacg    26460
aaatgcacaa cgtccccgac ttgaaaaacc cgatcactat gctatcggct gataccggat   26520
cactcgaata taacgtaaac gaggaaaaga ggctgagaga ggaacttgta agatcgcgataa  26580
cgggtggaga aggggaatta aataggtctg aggctattaa cgaaaagcaa gttaaagcag   26640
gctttgagtc catgactact aaactaaaca gaatcaaacg aggctttgag gaagcgcaaa   26700
cattcgtaga ctctactatc tgtttactcc gttatggtga tagctttgtt tcttgcaaga   26760
ttaactacgg gactgagttc tatatctata caccggcaga gctttcagag cgttataaga   26820
taatgaagga gaccggagcg tccgaagcgg agcttgacgc cttaaggcaa caaataatcg   26880
aaacggaata ccggaacgat cctacgcaga tgcaaaggtt attaatcctt aacgagatag   26940
agccttattc acacttaacg agggaagaag cggtaaatct gtataaagaa aacgttataa   27000
gtgaggaaga tttgcgagtt aaattaaacc ttcctacatt tgtgcgtaga tttgaaagag   27060
agaacatgaa tatcattgag ttcggttctg cacttgacta taaaaagaaa attgaaataa   27120
ttattaacac tttaaaaaag tacgcaaatg gtttacagaa cggatcagtt agatcaactg   27180
aatgaaagta attacgtttg cccgcaggat gaagttaaat tgtatcacgt tatccaagaa   27240
gtgaaagaat ttaatccgaa aacagggcaa agaatcagcg tcccggtgtt acaaaaatac   27300
aagcgaaaga cttttgaact tgatattttg ccgagactgc caagattggg ttatacattg   27360
agaattgttt tcgacccggt taaatatgaa tctacaattt cagaggcaag acgagccgca   27420
ggactggcag cgagagccga ggcaaaaatg aaggcagacg aagaactgag agagcaaatt   27480
agacgtgaag aagctgcaaa acttcgtgcg gagttgaaga aacaaaaaga gaaaggagaa   27540
aagtaatgtt aacagtagat ttgcttagac agaataaagc gttatcggag ctatcggatg   27600
aagttcttaa cgctatttca gaactttcaa aaaacgatga agcgcagacg gttgcggcaa   27660
aggtgagaga aaccgaaaac agtattgcta ctcaaatgaa ggaggctttc ggtattgaag   27720
gtgtaaccga tctcgatttg aaaaaccgaa ttgagttttgg caaaacaaaa ctttctaaat   27780
ctgataccttc agcttttgaa aaacagatta acgatctgaa agaagaacta aaagctgaga   27840
aagctaaaaa gggaggcgac cgggatactg ataaaatcaa tcagcttaca gccgaactaa   27900
acgacaccaa gcaaaaattt gctgagttga acaaccaact ttcagagaag gaaaaggagt   27960
ttaacggtaa gttgaacgat tacaagatca cttcttacat ttcaagcgca atgcagggga   28020
tgaagtttaa gaaagatatt tcagagccag ttttaaacgt tgtgaagcag caggcggtta   28080
acttgcttaa aactcaattc tcaccaactt tgcaaggtga cgaaggttct gaaagtctta   28140
tctttatgaa agatggtgtt ccttacaaca accctgcaaa tagtctgaaa ccgtttaccg   28200
catcagaact tctgtctcaa cagtttgaac agttcggtgt tcttgcaaga ggtagacag   28260
caggaggtgc gggtagttct ggaggcggac agggtaacgg tagcttgctt gatttaagcg   28320
gttgcaaaac caaagtagag gcaaacaagg ttgcgcagga gtatttagct aagaaaggtt   28380
atacaagcga gtcggaagag tatcaaacgg agcttgataa aatttgggtt gaaaacaaga   28440
tcgcagattt gccaacagaa taactaaaga gggggttaaa cccctcacaa tataaacttt   28500
aaaacaatag atttatgtcg ttaattgcta caagaacaca ggagttcaga ttaaagaacc   28560
ctaacattga caaaaatatg gctcgcatga ccgaatgggg tgcgtatgac ttctttttgt   28620
ctcaaacaaa tgcgatggac tcaatgcttt ccgatgaaac taagcgtaga gcgttcgcct   28680
cgatgggaag cgatattaag attcccgtaa ttgattacga taaaaacgta acagtgtcaa   28740
acgctcgcac atgcgttatc gcagatgcgg aaaacacttc acgtttgatc ggtgtaacgt   28800
ggaaaaccta tgctttcggt ttcactatga caccgaacat gtattcaaac aacgaaatcg   28860
attaccaaca ggactggaac agaaagctac aaaagcacat ccgtaagttc atggataccg   28920
ttgataagga cgctattgcg gctttggagg caaacaaaac acaggtattc ggaaacttgc   28980
tgtattacac aaaaacgggt aacgatgtgc aagtgaaatt cactcagcgc aacgacatcc   29040
tcagcgactt gcacccgatg ttccgtgcaa acgactattc cggtcaactt catatcattg   29100
gcgacactgg tgtagactca atgttgcgta aactggaaca gcacggtttg tacaatgacg   29160
ttaacaaaca gttggagtat gcaaacaaag tgttccattt caccaacaac atgactttag   29220
agccggaaaa cttcgctcag atgtatgctg ttgaatcgtg taacgttggt ttgttgaccc   29280
gtgtagaccg tgcagcctac aacaacacta gtcgggcac gcatgaattt ggaaaggttg   29340
ttcttccttac tttcggtaaa gaggttgaa cacactacta cgaagaagtg ggcgatcagt   29400
cagcaatcgc aggcgcagct actgccgata tgacttgtga cgttaaacat ttctacggtt   29460
tctcagtgga tattgctttc gttgtagcgt ttaactctga tccttcaacg atcgctaacc   29520
cgattatgaa gatcgaagta gcgaaagaaa attctcagtt tggcggaact ccggtatttta   29580
tcaccaatgc agatcagata ggcggaggtt ctccggctgg cgaattatcg gttaaccttg   29640
ctaaaatcgg aggtagtccg gttgctgaat ctgccttgaa agtagatttg gataaagtca   29700
aaggtacagc ggtttcgggct actggtggcg tagttgatgt taaagtcaat gcgcaggctg   29760
caaatctgaa tgttgaggtg aagaactctg aaagcgcacc tgtaccaaca aaaactgttg   29820
gcggagcgta acgagaaagt aaactaagta ttaacaaagg gaggggaca aaatccttc   29880
ccttttttta tttataacca tgtacagatt aaaggatata caaaaagaac ttgccacgct   29940
agtaggatgg aggcagtcgt acgatagaga cgctaagata gacgaaagtt taacggtgtc   30000
cgatagtggt gttatgtttc aagacgttca cccgcttgtg agctaagaa acattgaatc   30060
tattatgcca cttgattact atttacgtta tccggagtat cgggataccg acacttataa   30120
gccgggtgac aagtagttt acggcaagga cgtgttaacg cttcgtccgg acgtatggga   30180
ggcaataaca gagaatgttg gtgtagagcc ttccgatggt gataactgga aacggtacaa   30240
cccactaagc gattatttgc gtgaattgaa cgaaaagagc atcaccaata ccgttactcg   30300
cttcattaat gaaaagttga ttgcaggga aacaaagacg cttttagagc gtacaaactt   30360
ctttgatggt tcggggaaga taaataacga gattgaccct accgatagta ttgtaggata   30420
tgaaatattg ccagtccgtt ctatgggagt aacagccaag atcgagaaga taggtttgca   30480
gtttaacaag ccgggaaggg taaaacttta ccttatgcac acctcacagg tagacccgat   30540
taagacgttc gatttgaatt atactaaaaa tggttcttat caatggtttg atgtcggtaa   30600
tcgttgtta ctccccttata tgtctgagga acctcaccc ggtgtttgt ggtacttgtg   30660
ttacgatcaa aaaagaattgc ctttgggtat gtatgctata aacgtatcta aggactttc   30720
acgtgacccc tgcggtactt gtaatatcgg aagtgtgccg gcgtgagag agctaacaaa   30780
gtatatcaga gtgtcgccgt atagagttga ctctacgcag tcggaggatg gcgtaaagat   30840
gtggaatata gaaatgaaca tgtatacgtc tgcaatctgc tacggtttaa acgttcaatt   30900
gtcggtaggg tgtgatataa ctgactttat cattcagtct aagtatgcct tcacgcatgc   30960
```

```
cgtttctctg caaatggctt cttatgtgct gcgagagctt gcattaaatc cgaacgttcg   31020
gcaaaatgcc aatcaattga atattgaccg tgaaacgcta ttgtacgaag ttgacgaaaa   31080
ctcacaggga cgtgcgcagg gtatcggata cgaactaaag aaggcttttg aggctctttc   31140
tattgataca aaagggatgg atagaatatg tctttcttgc cggaacaacg ggataagatt   31200
taaagcaaca tgataagcgg tctaatagat aagtttaaaa aggtaggtga ggaactcgac   31260
accggagaga tagcaaaaaa gattgtgcgt gacaatgata atatacttat tgacatgaac   31320
gcacaagatc agctatacgc caagggtgtt aaccgtttgg gcgttcgtat agacgaatac   31380
cagcccctacc gaccccttaac tatacaagtc aaaatagaaa agaggcaacc gtacgaccgt   31440
gtgacgctaa aagacacagg cgagtttttac gactcttttt atgttgagac agcagaagat   31500
cggttttaca taaaagcctc agatgaaaaa actaattggc ttatcaaaaa atacggtgct   31560
gagattttcg ggtaacaaa tgattcactt gctgagttta ttaacgatta tgtgaaggac   31620
gaagcatata acagagtaaa ggagatatta aatgaacgat agagctataa ttagaccaaa   31680
tgcggaactt ttcgataaaa cgatagccga tgtacaggta agcctaacaa aatcgcttaa   31740
atggcttaat ttcgctttcg ggaacgtggt taaattggta gagagaaacg agagggggaa   31800
atttgttacc ccatcagtgt atttttaaggg aaatgattat ttgcgcttag agccggacga   31860
taagcggggt aacgtttgct ttttctacat gcacgactca caagattacg aaggggggaga   31920
ctctttatct ggctttggcg atctgagggg gacggttagc attatctttt ggttcgatac   31980
tcgtaaaata gcgggcgcag aatattacaa cgtggagttt gtaaagtccg aaatactaag   32040
agcattaacg catgaacttt atctgccatc cggtgatata caggtgagaa agatattcca   32100
cgatgccaac aacgtataca aggagttttc tatccaaaag acggataatc aatactacgt   32160
ttatccctat gcgtgtttgc ggtttgagtg tgatattcat tgcgaagaag ggtgttatta   32220
aaggggggagt ttcccccttt ttgtgttaaa tacatgttaa aacttaaagt ttcgcttgca   32280
atattaaata aagtccttat atttgcaatg tcaacaacg aaagaccccca caatctaacc   32340
aagacgcaaa aagattgttg aaagattaaa ttcataagag tagaaaataa gcaacggtat   32400
ctacgaaggg ttaaatgaag gttcggtatc cgattaaatg aagctataaa gcctaaatct   32460
ttcgaagtat gacaaattat gtagtaacaa ttaaaaatca agattatgac agcaagttta   32520
tttattcaga gaacagttga aaaatttatt atgatggaat ttgttaaggg aaacatggat   32580
accaaagaac aagttgatac aatgatagaa gttatcaaaa gaaagttaga cttttcgcat   32640
gatgaagcat gtgattttat aagaaaagcg atcggaataa acgaataact ttaattattg   32700
acaggtgggg ataatacccc acttcctaaa ataaaagcca tgaaagtaga taagtatcta   32760
aagagccaca aggcaaacga attttacgtg aaaaagtgta gaggttatta tctcgttatg   32820
gataactatg ataaaagttt ggcgtctatg gaggttacag aagaagaagc taaaaaggta   32880
gccgaacaac ttaacaagat tcgcaacgaa agattgaatc taaccgttaa ataatagtta   32940
aatactaaat ttaaacttgc aatattaaat attatcctta tatttgcagt gtcaaaagga   33000
aacaaattac taacaattaa aacccaaagt tatgaaaaga tattttgtaa acggaaaaga   33060
gataagcgaa caaaaagcaa aagagattga agctaataat aaaaagtata tggaaagcaa   33120
tgacctttct ctttgggcga aatgtgaatt tataacagtt attggaaagt aaaacaagtg   33180
ggggtaatac cccacataaa aattaaaaat atgactactt acatttataa aggacaaaag   33240
ataagccact ccaaaatatt atccctattg cgtagtgcag tgtatttacgg aggaaacaaa   33300
ctatcatatt atgaagtttt ggttaaagct gccgagaacg gcaacgaaag agccacatat   33360
attttgagag acttaaaagt gatataataa ccgtgggaaa ccacacaaat tttaaaggta   33420
tgtttaacga ggaaagaatt gagaatttag aaaaagagaat ttcaagaatt gaacagattc   33480
aaaatgcaga atgtaattct gcgcaaatga aagaaggt tcaacgtgct ttgattgatt   33540
ccaacaacga agtagtaaga agaatttttg atgatgtgtc cgttagttct gtatatggta   33600
tagatgtatt ttcaccgaaa accggagata ttcaagtacg taatgcggtg tttagtggag   33660
aggtattcaa acaagcggtg tctaacggta taccagatta ttttaaagaag gtagaagagg   33720
ataagacaga agcacctacc attgcaagcg tgttggaaaa agcaagaagg aatacgattg   33780
cgatacagga gctttaaaa cgaacaggat gttcgaacgt gaacgaagtg ataagcaagt   33840
ttgaacttgg agtttctttt aaaaagatgt atgatgaaga agcacgcaaa agaaaagagc   33900
ttgcacggca tagagatctt ttagattgtg atttaagaaa tcaaatagct aaactttctg   33960
ataaaaacca atctttgatg caaagtgaaa aaagccttat ttgcaaactt gcagacaaga   34020
acgaggaatt aaagagagtg gaagaacttt cagacggtag atataaagaa gtcgtttggc   34080
ttcgtggcga actgaaaaat caagaacagg cggtagaaaa actaaagac gaaaacaaac   34140
agcttaaata tgataatttg aaaatggaaa aagaacgtt agattccatt tgcggggaat   34200
cggatgcggt agtaagatat ttagatttga aaaagagata tgaagatttg agaaaaaaag   34260
aaaaaacgtt gcttgattct gtgcgtgaac tacaaaaaca agtatatgat gtttcgagag   34320
ataaaaaata cttggagata gcaaacactt cactcctaca agaaactcgt aaaacaaaag   34380
atgttttaaa cgagaaaatc aagaagctaa gacagagact taaacaatca tctatccgtt   34440
acagagactt aaaagaaagc attccgcaca acggtttgaa atcagtataa caataacagc   34500
cgggataata tcccggcaca atattaaaag atatgttgaa agtagatttg cgaataaaaa   34560
agatagagcc aaaattaggc gatattataa gtgtcgtaga ggaaattttt acaacgatag   34620
taaaaactat tccatacgag ggagggactt gtcaaggat gctttttat gatagagta   34680
atgtcgattt agattgcccc tatttcgtta agtgtgttaa gaatagagtt atgtttaaac   34740
taataagaaag aaaatgaact aaggaggtaa aaaaatgaat atacacatt tgtcggatag   34800
agatatattc gtaccgaaag agggtgaagt attttttgta gaagttccgg gaaagggaat   34860
agaccggaag gtagaggcgg tattattgaa aggcaatagc ggttgcaaga attgcgcatt   34920
ttttaaagga gaattaaaag acttgtgtat gcaaataaac tgccttaaca gaggaaggca   34980
attaactttt aggagggtga aaaatggaga aatttaaaag cgtagaacta tatgatacct   35040
tcacgataga tcacccgata acaggcgaag ttatcagagt tcaagcaata ccacgggata   35100
ccatttcatg caacgatgt gccttccgaa agggagattt agaagggatg tgcaaggtat   35160
acgcatgtgt gaacaatcaa acattagatt gtttagtgtt caagaaagta aagtagaaat   35220
taaaacgaaa tgttacagag ttttaaaagt taaagtatta atttaaatgt gttgacttat   35280
gaaagaagaa gttgttttaa tgctctctga gctaagatcg caaatagatg atacaattag   35340
tcgtgttaag aaagaaatcg ccttagatgg caaaagaata atgtctacgt tggaaggttg   35400
tggcttgatt gagatatgca attatttaat ctcccgcaa gccttttag agtggtgttt   35460
tagccgtgga ttttttggaga cggaaggtga ggtatttact gtcggaggga atccctggat   35520
agggaataaa tacgtttcaa aaaacgatct aattaacttg gataaaaacg gcaatttgtc   35580
cgttcatcct tcgttgctgt atgtctattt aaactgttgg aagaatgaat aatacaaagg   35640
actcatatat cgacactaag gtatacagcc tcgcaatagc ggtgctcgat atggaagatt   35700
```

```
acacgaagtt tgaaaagtgg cttatttaca aagaatatat aggatccccg tttgatggta  35760
aatacactcc attagatcac agagtgaaaa tatcatcttc tggtaatata tttgttactt  35820
ctgacttgat taatacgttt tatgcctgca atggaattaa taaaatcatg ttgtgattag  35880
gaatcttcgg attcctttc ttatttataa acattttgtt tttatccgtc ttcggatagt  35940
ttgagactaa cgttttaata atcaaatatct ttgcaaaatt gcttttttatt catcttttg  36000
tacaaactaa tatttgaatt atggagattt ataattattt tctttcttgc gtgctacttg  36060
tttcgttgt agcggcattt tgtgttaact ttgcccgaaa gacgggtgta attgaacgga  36120
tgtcagtgtt cggtgacgct tggttatcta aggtgttccg gtggtatggc gatagatcac  36180
ttattaacga gctaactaac tgcaatttct gtctatcgtt ttgggcatgt gttatttgtt  36240
cggtgattgt gtcggtcgga acgctaaacc cggtgttcat ccttacaccc atctttgcaa  36300
cacctatttg tagaattta atttaatgat tatggaaatt agaaattatg tatcggttat  36360
accacctttc gagatcgtga aggcggttaa gtttaacggt gatgttcacg aattagcgca  36420
gctattgcca agttttgaac tgctttccgc aatggatggt gtgatgatgg cacgaataaa  36480
tgataacgct ttccgtgtgt ttgataacga ttatatcgtt cttggcgaaa atgttactta  36540
ctcagtcgat gaagaaacgt ttgccatatt atacgagcag gcagataagg aggtgacgaa  36600
tgaacacgat taaggtaggg aatcacacgg taacggtata cgaaggcatt gacgaaatgc  36660
ctatcgtccg ttatcaaaag ttcaaccgtc ttatgttgat tgagtcgggt gttggaagca  36720
ctatcgagga actcgacacg catttgcaac gtgctattgt ctattgcagg acacgaccgg  36780
aacacacgta taacgagcta atgaatctaa ggcagtgctt taatatggca gcgaatggcg  36840
tacatcccgg aatgatggct tttgccgcct tcgttaagtc ggtcgatggc gtggaatatc  36900
cggttaacgc atccgactct gatctaaagg cgatatttga cagcctcagc gatgcaacta  36960
ttaacgaact ttctgagccg tttcagaagg tcaaaaaaaa aatagaggcg gaagtatcga  37020
tatactttcc aaggatggcg gacgatcctc tgattaaaga gtattacgat attaaattat  37080
cgctgataaa agcaaagtta gacaaacttt gaacaacgt agataacagt gaggcggtga  37140
aggaaataga ggataagtta ctaaccttct tcccgcctcg aatattctac ggaactgatt  37200
cgatcgaaat aaagacggat aaagagtttc aagaaatgtc cttggtaatc acgcagaata  37260
tgcacataaa tgcacgtgaa atgtcggtgt ctgagtttta caccgctttc gagatgatta  37320
agagaccggc aaaaaggagt aagaacaaat aaatttaaat caaatggcga acgaagtaaa  37380
gggaataaag tatagcgatc ttatacagcc tgacagcagt ataaaggacg ctattacgca  37440
gttggaagga ctgcaaaaga tatatgactc tatgttaaga cgtatcgagg aaggcgcaaa  37500
aggtctgcaa aagcctattt cagaaggtgg aggcgcaacg gaggaagggc gcaaaaagat  37560
agacgcctac gaaaagcaag tgcgatcctt ggcgaacgct gagatacaat tgaaattggc  37620
gttgacagag acagcgcagg agatagcagt cttaaagaaa cagacagccg atcaaaacta  37680
tctgaataag ttgcaggcta agttagccaa cagcatggca ggaagctata acgcattgtc  37740
tgcacaatac gagctaaaca aataaagat gaacaatctt tcacaggctt atttggagaa  37800
tacgaggca ggaaagaagc ttgttaaaga gactgcggag atttacgcag cgatggataa  37860
ataccaaaag agcacgggaa agcacacgtt aagcgtgggt aactcaaaac aggcgttcga  37920
tggtttaggc ttttctatat cacaggtcgc tcgtgaactc ccatccttgg cgatcagcgc  37980
aaatacccttc ttccttgcta tttccaataa cattccgatg gttatagacg aaatacagaa  38040
gttgcgtgcg gcaaacgagg cggcagcgaa agcgggggaa gcacaggtaa gtataaccgg  38100
gaaactggtt aaatctctgt tctcgtttaa taccgtgatg gtgttgatat tgaccgcctt  38160
ttctatttgg ggtaaggata taaccaactg gataggtagc ctattcaaag gtaaaacaac  38220
agtagatcaa ttgaaacggt ctactgccga cttgaaagac gccatgttag aggctggaaa  38280
gagtgccgta aacgagtctg tgagactgaa catcttgtat aaagcggcta ccgattccac  38340
gcgcagccaa aacgagcgtt tgaaagctgt taaggagcta aagaaagagt atccggatta  38400
ccttaaaaac ctctctgatg aagctattat gacaggaaac gcatcaaagg agtataagga  38460
acttgcaaaa cacattctat cggtagcaat ggcacgtgcc tacgaggaaa ggatacaaaa  38520
gaacgccaag gaagttattg acctcgagga aaaaaagaac caagtattag aggaaggtcg  38580
gaagacttac caaaagcaac aaaaggagat cgaggaactt aaacgttcgt ctaagggtat  38640
cggtgttggt gcggtggctt tggaagcggc tttgcaaggg caagcgtccg catggaatac  38700
cgccaaaaag gaggcaaaga gctatgacga acaaatagca gttatcaata gtcgagtga  38760
ggaacttgct aaaaaggtgg ttatccccga tcttccttgca ggggacaaag gaggtaagac  38820
gaaggaaagg acaagaagg actttgatct acaagctgag tatgaaaata gccgtatagc  38880
tcttattatt gattcacgtt tgaaagagca ggaagaacgt aaaaaggcaa cggcagatga  38940
actgaaaaag ctaaaggaga gcacaacaga gaaacaaaag gctacgcagt tgtatgctga  39000
taccgtatac aatatcgaag caaagttgcg tagagatttg gagaaactgc aaaacgattg  39060
gaaggtagag gatctgcaaa tcacgcatga ccgattgagt gaacgcctaa aggctgttag  39120
acgtggcacg gctgacgagc tattaataca agtgcagtta ctcgaaaacg aaagagcgca  39180
ggacgaattg cgtattaaac agtcaaccga tagcgaacag gtgaagaatg aacgtttgct  39240
tattctgcaa aggtcgtatc agcttgcatc tatccaactg caaaaggatt tcacggaaaa  39300
tcaagacaag cgtataattg atcggtcggt gttccgactt aatcagcaac agcaggcgga  39360
aagtgcagcc tttaatatcg tgcaacgttc ggagaaagaa cagagccgtt tccggttgaa  39420
attagagcgt gaaaagtggg agcaaatatt agagttaaca aggcagtacg gagagcaaat  39480
cacgggatac aacgtaaaga cggtagagga taccattaag gttaataagaa atgcaattaa  39540
gcgtgatact tccggatggg acagcaatca aggcgtattt ggcaatctgt ttgatcttgt  39600
tttcggtgac gcatttagcg ctaaaatgg taagtcgggc gcagagctg ctgagcagtt  39660
taaagactcc attttagagg cttcggagtt cgccatagag aacctaaaga gtgttgcaca  39720
ggcaagggta gaggcggcag aagtggcggt acaggcagca gagaaagaag tatcagccag  39780
acaaaaggtt ttggacgctg agatacaagc gagggcgaac gatacgcca acaacgtggt  39840
aaccgcacaa aaagagcttg attttgcacg caaacaacag gaaaaagcgc tgagggataa  39900
gaagaaggcg cagaagcagc aagaacgcat agatacactt atgcaggcaa gttcttggt  39960
aaccgcaacc gctaacctat ggaaagattt aggttttggca gcgatccgg ctattgcgtt  40020
gatgtgggga tcatttgctt tgctaagat aaagctccca cagctatcta aagcctcgca  40080
gaggaacaag gatacagga acgtggcggt agaaatgatt gattacggag gttgcgacag  40140
atccggaaac gatgtagatt taggtacgac taaggacggt aagcgtagac gggtagaacg  40200
tggtgaatac ttcgcagtag tgaacaaacg ttcatctcag aagtataaga aactcgttcc  40260
ggacttgatt aattcgctaa ataagggtat ttttgaacag aaatacttaa acgcctattc  40320
cggtagtgat gaagtaacga atataatgca aggttcaacg gttgatctgt ctaaggtcga  40380
aaagatctg aaatcaatca aagagcaggg acgtgttaag tacatcacag gtgcggacgg  40440
```

```
cacgataatt gaagtaaggg gaaatattaa acgaataatt aaatcataat gaacgttaaa   40500
gatttgcggt ttaaattggg gggtgtagaa atacatcccc actattcaga gctaaaacgg   40560
aagtttggca aagagaatca acaggagttt ttcagagagt cgatagaggg gagtttaacg   40620
ctgatagggc cggactacct tcttgttaaa aatgcgagta ttgaggatat tttgtacttg   40680
caaatagagc aaaaggataa agggcagcta tcaacgcagt atcaagtaat atttgagggc   40740
tatttcagta agacagactg tgagatagac agtgataacc ggacgtgcaa ggtgaagata   40800
agcccacgtg atgaatacac cgatattatg aagggaattg agaacaaata tgatcttatc   40860
aagcttgcac ccggcttaac acaaataggc gtgtctaagc gtcctattgt tcaagtttat   40920
attgcaggtt cgcctacaat atcaaactac cttgcaggaa ctcactacga aactgaggtt   40980
tcaaacgttg taactgataa caaggaatta acggacaaaa atttctttgc cttctttgct   41040
gcatacaacg aagtggaaat aaaggcattg ccttatcagt cttttaacgg gaagtattac   41100
ggaacgaacg gtaattattc aaaattagac ggaaactata cattaacatg gaaatatgta   41160
gatttgagtc aaggttttt agtgcttaaa aacaggaatg gagataggct ttttaggtca   41220
aatgcgcttg tttgggggaa taagaattat ttctatatag acgcttctga gttaacattt   41280
acgaggttag tagaagaacc tacatttcct cagtcgttcg ggggaaatac ggtattactc   41340
caaaaggtat ttcaaagaat gttgcttaac cttccggagt tggacggtaa acctactggg   41400
aaactatcat cagaggacgt ttaccctacc aatagtaact acatgtatgc cgcaccatta   41460
aaggggaact acttttatac gtctacgaag gttcagaacg agccgacaga gtacggtgta   41520
aatgatgaag gcaagtattt taccgataac ttccgttccgg ctgtggcggg tgctggaaag   41580
ttgtatccgg tatgccgttc acgatggggg aatatgtcga tttggttcga gtttgatttg   41640
tcctatgcgc cattggagga aagagcgaga aaggagtatg ttttaaggga ctcgttcgcc   41700
atacaggacg ctattagggc gcttattaag caaattgatc ccactttgac gcacgaagct   41760
acggaggaat atagtaagtt tttgtatgcc ggcaataacc ctatttccgg tgcaccttt    41820
aaggtgttca tcacacagaa aagcaacatc ctaaagggtg agtatgaccg tccggcaaaa   41880
aaggcggaaa caaccctcag cgatataatg aagatgttgc gtgacacgat gaaactatat   41940
tggtttatag atggagataa gtttaggata gaacatattt cttacttcat gaatggcgga   42000
agttataccg gtagcgggac ggtcggcata gacttaacaa agcttagata tgcaaaatcg   42060
ggtcagttaa tgacgtggaa aactaacacg gtcaaatatg ataaaaccga tctgccttca   42120
cgcttttgaat tttcttggat ggacgatacc acaaatacgt ttgcaggttt tccgattgac   42180
gttaaatcaa actacgtgca ggaggaaaag aaagaagaag taagggtatc taacttttcg   42240
tccgatgtag attatatgct actgtctccg ggtgacttt cacaggatgg ttttgcgctg    42300
ttgggagcta tacaggtgag tgggaaatgg aaacttccgt ttgttacgtt caatttggta   42360
gacaagaaca ataataagta taccgtaaac ccccaaaatg gctatatgtc gttccttcac   42420
ctcgttaaat actacatgta tgatatgcca gccttagaga ttgagcacgg aggcgatcag   42480
acggtaaggg tgagaggaat aaaacggagt atgacgcaag atttatccTT tacatacgac   42540
accacgccaa acccggtaca actgataaca acggatgtcg gcaacgggaa accgatctct   42600
atgactgagg acttaaccac ccgacaaata accgtatctt tatcttacac ccccttatga   42660
taggggggtgt tttcttttaa attgctatct ttgtccctat aatcaatttt ttaatcaaaa   42720
tggaagtaca taacaactt agtccgttgg catttagaaa gaaggaatct aaagccacat   42780
acgaaaaatg gtacgcttc gggaagaact acgctattcc tgcaagcgca aacacgctaa    42840
ctcctttcca gtttacagag ttgaacatac cagtctttga ccccgatacg atcgaagtag   42900
atgcggttaa cgaggaaacg ggagaggcga caaaaacggg tgtatatgtt agcttcgatg   42960
ttatgcccga acatggtggt gttttgtacg tgtcaccagg caagaactcg tttagggagg   43020
ctttgccgca ggggacgtat agagcacgtt tttcaatcgg tgatcaagta tatatttcga   43080
ctcctttttg cgttataccc ggcatagaaa cgagtagcaa atatctattg attgaatatt   43140
ggaacgatga aaagatcgtc tatccggatg gctttattac aacgggtacg aacaatgact   43200
tccggtatca gatgtatgtt cctgcaacta tctgcaaacc gaaatatgag tttgaagaag   43260
aactaaccaa acgcgccgga tacaagttct tagaactgca aacgtctacg aaggtgtacg   43320
cctttacatt tgttgcgcct gagttttattt gtgacgctat gcgactgatc cgcctatctg   43380
actatatccg aattccgcac gatggcgaat attcaacgc cctcaacttc gagtttgatg    43440
ttgattggca ggaacaattg tatttggcgg ctgttgactg ccagtttgag acggactcaa   43500
tcatacaaaa actcccttct ttcaatagac gagataaagc gtcttttttat aatgccctat   43560
tagcgaacat tgcacacccg ataatgttcc ccccgatac cgtagggctg tattacaaag   43620
agtatcggga aacagagcca gttgtcaaag gtaaattgat ccgtgaacta tcaccgattg   43680
atttgattga cgaaaatacc actattgccg tagatatgg tgcgggtgag gcacgcaaat   43740
tcaaccttta ccgcatgttg gagggataca tctctaagga cccacgaagat gtaacgagt    43800
tcctttatc ccttcgtgga ggcgtgaata tcggtacacc gaatgcaagc ggtgagtatc    43860
ctgcaagcgt agacaggtac gggaacgcta agttaaagga catacagggg aatgatgcaa    43920
cgttgaacaa cgtcacagga aaagaagcta cgtttaaaac tgtggaaacc ggtttcttaa    43980
ctgttaacaa gacttccgca acaattgacg gaatgggtaa cgccaatgta accgatttaa   44040
ctgcaagggg tgactctatg ttgcgcagcg acgtatatac agggtcaaaa aatggcagtc   44100
ataccggaaa gataacgaaa gaaggacagt tgcagtatct atcagctatc atttacgagt   44160
tcctttcgtc cgaaacgttc gttccgggct tcttaggtga aggcttttaaa atatggttgg   44220
ataatggtaa ttggcatatc gaatgcgata acctaaccgt ccgccaaact atgaacctt   44280
ttgagttgct tatccaaaag attccgcagcg tcaacggtgc tattgtcgta tcccaatcaa   44340
acggtaaggt tacagccgtt gaggacaccg gaacacagta caaaatcacg ttcggagagg   44400
aatttcctac cttccaagaa ggtgacttga tacgctgcca atcgtggagt aagaacaaca   44460
ttaaattcta ttggggtagag gcaaagacag ccgcagacgg ttatgttctt tgcgataagt   44520
ccgagttcaa caacgttgtt ccggctgttg gcgatgaagt tgtgcagatg ggtaacacga   44580
agaatgccga aagacaggct ttgatctata ttacagcgca ggaaagcggc aaaccgtaca   44640
ttgagattct gaacggtgtc aagacaaaga gtctgaccgg gacagaccgc acccgtcttg   44700
gcgatttgtc taacattgta gaccccgatt ttacaggtga ggcggctgtg aaagggaccg   44760
gtttctattc tacgaatgct ttcttgaaag gtatctttgt attgcgcaac ggaaagcgtg   44820
tagaggcgaa aattaagatt gcaaaggacg cagcagacca agcggaaga gacgcagcga   44880
acgcagcaca atcggcacag gaagcgaaag ataggcttaa caaatgggca gacgatggat   44940
ttatttcacc gactgagaaa cctgcattga ttgacgaggg gaagcgcatt caagcggagt   45000
atctgcaaat aaaggcgaat gcggacagt acggtgttcc tgtaactgaa tatacgagg    45060
cgtataacaa ctatccttaac gaactacgtt atcattcggc tactacacct gaaaatattg   45120
tcgtgcgtcc agaattggca cagagccaaa cggcttacta cgacaaacgt aatggagcgt   45180
```

-continued

```
tgaatgcaat tgctacggct tcaaaagaat atgtagataa tgctgacaaa aagttaaagg    45240
aatacttaga tactgagata actgctattc ccggtaagat tgaacttgct gtacggagtc    45300
tgaaaacggc aaattacaac ttgctgttag atagtaacca cactcttagc gaaaacccgt    45360
atcagcttgg atcatacaaa tatgatgttc atttggtgaa aggtaaatct tatacgttga    45420
ctgtttgtta caagtgtgca gattcggacg atgttgtagc gt                      45462
```